(12) United States Patent
Dickson et al.

(10) Patent No.: US 12,061,143 B2
(45) Date of Patent: Aug. 13, 2024

(54) METHODS FOR RAPID DETERMINATIONS OF ANTIBIOTIC SUSCEPTIBILITY PHENOTYPES

(71) Applicant: Georgia Tech Research Corporation, Atlanta, GA (US)

(72) Inventors: Robert Martin Dickson, Atlanta, GA (US); Tzu-Hsueh Huang, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1076 days.

(21) Appl. No.: 16/477,260

(22) PCT Filed: Jan. 12, 2018

(86) PCT No.: PCT/US2018/013529
§ 371 (c)(1),
(2) Date: Jul. 11, 2019

(87) PCT Pub. No.: WO2018/132680
PCT Pub. Date: Jul. 19, 2018

(65) Prior Publication Data
US 2019/0338334 A1  Nov. 7, 2019

Related U.S. Application Data

(60) Provisional application No. 62/445,518, filed on Jan. 12, 2018.

(51) Int. Cl.
| | | |
|---|---|---|
| *C12Q 1/18* | (2006.01) | |
| *G01N 15/14* | (2006.01) | |
| *G01N 21/39* | (2006.01) | |
| *G01N 15/10* | (2006.01) | |

(52) U.S. Cl.
CPC ........... *G01N 15/1459* (2013.01); *C12Q 1/18* (2013.01); *G01N 21/39* (2013.01); *G01N 2015/1006* (2013.01); *G01N 2015/1402* (2013.01); *G01N 2015/1488* (2013.01)

(58) Field of Classification Search
CPC ....... G01N 15/1459; G01N 2015/1006; G01N 2015/1488; G01N 2015/1402; C12Q 1/18
See application file for complete search history.

(56) References Cited

U.S. PATENT DOCUMENTS

2015/0064703 A1 * 3/2015 Super .............. G01N 33/56938
435/6.12

OTHER PUBLICATIONS

Faria et al. The development and application of a molecular community profiling strategy to identify polymicrobial bacterial DNA in the whole blood of septic patients. BMC Microbiology. 2015; 15:215.*
Gant et al. The application of flow cytometry to the study of bacterial responses to antibiotics. J. Med. Microbiol. 1993;39:147-154.*
Search Report from Application No. EP18738607.3 dated Nov. 23, 2020 (10 pages).
Cohen, et al., "Rapid Flow Cytometric Bacterial Detection and Determination of susceptibility to Amikacin in Body Fluids and Exudates," Journal of Clinical Microbiology vol. 27, No. 6, Jun. 1, 2989 pp. 1250-1256.
March, et al., "A New Approach to Determine the Susceptibility of Bacteria to Antibiotics Directly from Positive Blood Culture Bottles in Two Hours," Journal of Microbiological Methods Feb. 1, 2015, vol. 109 pp. 49-55.
Arabski, et al., "Effects fo Saponins Against Clinical *E. coli* Strains and Eukaryotic Cell Line," Journal of Biomedicine and Biotechnology Jan. 1, 2021, pp. 1-6.
International Search Report and Written Opinion from Application No. PCT/US2018/013529 dated Mar. 8, 2018 (9 pages).
Huang, et al., "Rapid Cytometric Antibiotic Susceptibility Testing Utilizing Adaptive Multidimensional Statistical Metrics," 2015 Analytical Chemistry, vol. 87, No. 3.

* cited by examiner

*Primary Examiner* — Lynn Y Fan
(74) *Attorney, Agent, or Firm* — Troutman Pepper Hamilton Sanders LLP; Ryan A. Schneider; Chris N. Davis

(57) ABSTRACT

The invention is directed to a method for rapidly determining antibiotic susceptibility in bodily fluid samples based on rigorous multidimensional statistical metrics. In some embodiments, the method incorporates flow cytometry to determine susceptibility. In preferred embodiments, the method is adapted for use with samples with low bacterial counts.

14 Claims, 14 Drawing Sheets

METHODS FOR RAPID DETERMINATIONS OF ANTIBIOTIC SUSCEPTIBILITY PHENOTYPES

CROSS-REFERENCE TO RELATED APPLICATIONS

This application claims priority to U.S. Provisional Application No. 62/445,518 filed on 12 Jan. 2017, the disclosure of which is herein incorporated by reference in its entirety.

GOVERNMENT SPONSORSHIP

This invention was made with government support under Grant No. R01AI107116 awarded by the National Institutes of Health. The government has certain rights in the disclosure.

BACKGROUND

1. Field of the Disclosure

Embodiments of the present disclosure relates generally to methods for rapid determination of antibiotic susceptibility of bacteria in patient bodily fluid samples, and more specifically to such methods for use with low bacteria counts.

2. Background

Sepsis, a life-threatening immune response to blood infections (bacteremia), has a ~30% mortality rate and is the 10th leading cause of US hospital deaths. The typical bacterial loads in adult septic patients are <100 bacterial cells (colony forming units, CFU) per mL blood, while pediatric patients exhibit only ~1000 CFU/mL. Due to the low numbers, bacteria must be enriched through ~24-hr blood cultures to generate sufficient CFUs for diagnosis and further analyses.

Leading to many deaths worldwide, sepsis can result from <100 CFU of bacteria/mL blood. Such low bacterial counts limits determinations of appropriate treatments, even in hospitals with advanced clinical diagnostics available. Early appropriate antibiotic treatment for bacteremia patients not only shortens hospitalizations and reduces antibiotic resistance proliferation, but it also lowers the incidence of septic shock and halves the fatality rate.[2-6] As sepsis can be caused by any of a number of bacteria, effective treatment relies on the combination of bacterial identification and sensitivity profile determinations. While pathogen identification has been hastened to just a few hours post positive blood culture,[7-11] antibiotic sensitivity tests (ASTs) still require an additional ~36-44 hrs, post blood culture.[12] Although many flow cytometric-based ASTs have been proposed,[13-22] development of general phenotypic ASTs has been elusive, due to the wide range of bacteria and antibiotics interactions, biovariability, noisy fluorescence background, and lack of reliable multidimensional statistics analyses to interpret small changes within the heterogeneous populations.[17,19,23] These challenges have forced reliance on slow, but reliable blood cultures for amplifying populations, followed by multiple purification, growth, and antibiotic challenge cycles to guide treatment.

Developing ASTs directly from blood and circumventing the initial ~24 hr blood culture delay promise to drastically improve patient outcomes and impact public health efforts. Even though the ~$10^9$ mammalian blood cells/mL overwhelm any low-level bacteria signals (100~1000 CFU/mL),[24,25] bacterial presence determinations within blood samples have been reported by flow cytometry,[26] microfluidics,[27-29] and PCR.[30,31] While most of these schemes detected the presence of bacterial genetic material, Hou et al. was able to detect mRNAs after pathogens were separated from blood in a microfluidic device.[28] Like other molecular diagnosis approaches, however, they can only target known mRNA signatures for individual antibiotic resistance genetic markers for each bacterium-antibiotic pair. A phenotype-detecting flow cytometry-based AST specific for Y. pestis was proposed that relies on post-growth recovery of bacteria from a gel matrix and viability dye detection.[32] Generalization, however, is problematic as careful bacterial recovery, significant post collection growth to reach ~$10^6$ CFU/mL, and user-dependent data gating were all needed to overcome the high scatter and fluorescence background. Additionally, viability dyes are known to produce false signals with various important bacteria/antibiotic pairs,[17,19,23] and gating is highly subject to variations in day-to-day instrument fluctuations, alignment, and parameters, limiting application of this approach.

The inventors have developed a rapid, flow cytometry-based AST based on rigorous multidimensional statistical metrics[1] that matches the timescale of emerging post blood culture identification (~4 hrs after positive blood culture).[8-10] The inventors' adaptive, multidimensional Probability Binned-signature Quadratic Form (PB-sQF) statistical distances[1] were shown to be ideal for quantifying small, but statistically significant changes relative to paired controls, even within broad, multidimensional flow cytometry datasets. PB-sQF was used to calculate the true linear distance between any two multidimensional histograms, thereby enabling rapid direct comparisons of changes within heterogeneous populations, relative to their paired controls. The inventors' prior order-of-magnitude improvement in post-blood culture time-to-result could, in most cases, be done label-free, and with bacteria-antibiotic combinations that had failed with previous cytometric tests.[1]

Without blood culture-based amplification, the highly disadvantageous bacteria:mammalian cell ratio, even in patients with bacteremia, generally requires that phenotypic ASTs remove nearly all mammalian cell background, without killing the bacteria. Additionally, sufficient bacteria must be recovered to allow assaying with multiple antibiotics at various concentrations, suggesting that at least some amplification, or a higher volume of blood (at ~100 CFU/mL), is needed. Because time is critical in ensuring appropriate treatment for patient survival[33] and reducing antibiotic resistance proliferation,[6] it is also important that any AST can be completed in a relatively short timeframe, rather than the multiple days generally required for phenotypic assays and subsequent antibiotic susceptibility testing.

What is needed, therefore, is a method for rapidly determining the antibiotic susceptibility of various bacteria in a patient bodily fluid sample (such as for example and not limitation, blood, sputum, pus, urine, plasma, serum, cerebrospinal fluid, and/or saliva). The method should take advantage of advanced detection methods such as flow cytometry, while improving assessment of samples with high bacterial counts (such as for example and not limitation, at least about 11,000 colony forming units (CFU) per mL bodily fluid to about 1,000,000 CFU/mL bodily fluid) and also with low bacterial counts (such as for example and not limitation, at least about 10 colony forming units (CFU) to about 10,000 CFU)/mL bodily fluid, and be capable of completion within about ten hours, preferably within about eight hours, more preferably within about five hours, and most preferably within about three hours from initial sample collection. The method should provide improved susceptibility assessments based on use of statistical analyses or statistical distances including for example and not limitation, adaptive, multidimensional Probability Binned-signature Quadratic Form (PB-sQF).

BRIEF SUMMARY OF THE DISCLOSURE

As specified in the Background Section, there is a great need in the art to identify technologies for rapid determination of antibiotic susceptibility of bacteria in patient bodily fluid samples and use this understanding to develop novel methods for such determinations, including methods that can accurately determine susceptibility for samples with low bacterial counts and can be completed within ten hours from initial sample collection. The present disclosure satisfies this and other needs. Embodiments of the present disclosure relate generally to rapidly determining the antibiotic susceptibility of various bacteria in a patient bodily fluid sample (such as for example and not limitation, blood, sputum, pus, urine, plasma, serum, cerebrospinal fluid, and/or saliva). The method should take advantage of advanced detection methods such as flow cytometry for recording fluorescence and/or scatter signatures of multiple individual bacterial cells, whether in home-built, commercial, or microfluidic devices, while improving assessment of samples with high bacterial counts (such as for example and not limitation, at least about 11,000 colony forming units (CFU) per mL bodily fluid to about 1,000,000 CFU/mL bodily fluid) and also with low bacterial counts (such as for example and not limitation, at least about 10 CFU/mL bodily fluid to about 10,000 CFU/ml bodily fluid), and be capable of completion within about ten hours, preferably within about eight hours, more preferably within about five hours, and most preferably within about three hours from initial sample collection. The method should provide improved susceptibility assessments based on use of statistics including for example and not limitation, adaptive, multidimensional Probability Binned-signature Quadratic Form (PB-sQF).

In one aspect, the present disclosure provides a method for rapidly determining the antibiotic susceptibility of various bacteria in a subject's bodily fluid sample, the method comprising:

a) isolating the infected bodily fluid sample from the subject;
b) optionally diluting the infected bodily fluid sample with a bacterial growth medium;
c) optionally treating the infected bodily fluid sample with saponin;
d) optionally incubating the infected bodily fluid sample to allow for bacterial growth; and
e) dividing the infected bodily fluid sample into samples for incubation with at least one antibiotic and a paired control sample that is not incubated with any antibiotic;
f) collecting multidimensional data via flow cytometry of the infected bodily fluid samples incubated with the at least one antibiotic and the paired control sample; and
(g) analyzing the multidimensional data to determine if the bacteria are susceptible to any of the at least one antibiotics.

In another aspect, the present disclosure provides a method for rapidly detecting the antibiotic susceptibility of bacteria in a subject's bodily fluid sample, the method comprising:

a) isolating the infected bodily fluid sample from the subject;
b) optionally diluting the infected bodily fluid sample with a bacterial growth medium;
c) optionally treating the infected bodily fluid sample with saponin;
d) optionally incubating the infected bodily fluid sample to allow for bacterial growth; and
e) dividing the infected bodily fluid sample into samples for incubation with at least one antibiotic and a paired control sample that is not incubated with any antibiotic;
f) collecting multidimensional data via flow cytometry of the infected bodily fluid samples incubated with the at least one antibiotic and the paired control sample; and
(g) analyzing the multidimensional data to determine if the bacteria are susceptible to any of the at least one antibiotics.

In another aspect, the present disclosure provides a method for rapidly differentiating between the antibiotic susceptibilities of different bacteria in a subject's bodily fluid sample, the method comprising:

a) isolating the infected bodily fluid sample from the subject;
b) optionally diluting the infected bodily fluid sample with a bacterial growth medium;
c) optionally treating the infected bodily fluid sample with saponin;
d) optionally incubating the infected bodily fluid sample to allow for bacterial growth; and
e) dividing the infected bodily fluid sample into samples for incubation with at least one antibiotic and a paired control sample that is not incubated with any antibiotic;
f) collecting multidimensional data via flow cytometry of the infected bodily fluid samples incubated with the at least one antibiotic and the paired control sample; and
(g) analyzing the multidimensional data to determine if the bacteria are susceptible to any of the at least one antibiotics.

In one aspect, the present disclosure provides a method for rapidly diagnosing a subject with antibiotic-susceptible bacteria or antibiotic-resistant bacteria in the subject's bodily fluids, the method comprising:

a) isolating the infected bodily fluid sample from the subject;
b) optionally diluting the infected bodily fluid sample with a bacterial growth medium;
c) optionally treating the infected bodily fluid sample with saponin;
d) optionally incubating the infected bodily fluid sample to allow for bacterial growth; and
e) dividing the infected bodily fluid sample into samples for incubation with at least one antibiotic and a paired control sample that is not incubated with any antibiotic;
f) collecting multidimensional data via flow cytometry of the infected bodily fluid samples incubated with the at least one antibiotic and the paired control sample; and
(g) analyzing the multidimensional data to determine if the bacteria are susceptible to any of the at least one antibiotics.

In another aspect, the present disclosure provides a method for rapidly classifying bacteria in a subject's bodily fluid sample as being susceptible to antibiotics or not susceptible to antibiotics (i.e., antibiotic resistant), the method comprising:

a) isolating the infected bodily fluid sample from the subject;
b) optionally diluting the infected bodily fluid sample with a bacterial growth medium;

c) optionally treating the infected bodily fluid sample with saponin;

d) optionally incubating the infected bodily fluid sample to allow for bacterial growth; and e) dividing the infected bodily fluid sample into samples for incubation with at least one antibiotic and a paired control sample that is not incubated with any antibiotic;

f) collecting multidimensional data via flow cytometry of the infected bodily fluid samples incubated with the at least one antibiotic and the paired control sample; and (g) analyzing the multidimensional data to determine if the bacteria are susceptible to any of the at least one antibiotics.

In an embodiment of any of the foregoing methods, step (g) further comprises the steps of:

i) calculating an adaptive, multidimensional Probability Binned-signature Quadratic Form (PB-sQF) statistical distance for each of the infected bodily fluid samples incubated with the at least one antibiotic and the paired control sample based on the results of the flow cytometry analysis;

ii) comparing the statistical distance from the patient's infected bodily fluid samples incubated with the at least one antibiotic to the paired control sample; and iii) determining whether the bacteria in the infected bodily fluid sample are susceptible to antibiotics or not (i.e., are antibiotic resistant).

In an embodiment of any of the foregoing methods, the steps of treating the infected bodily fluid sample with saponin and incubating the diluted infected bodily fluid sample to allow for bacterial growth/expansion occur at 37° C.

In an embodiment of any of the foregoing methods, the step of treating the infected bodily fluid sample with saponin is at least about 10 minutes.

In an embodiment of any of the foregoing methods, the step of treating the infected bodily fluid sample with saponin is at most about 45 minutes.

In an embodiment of any of the foregoing methods, the steps of treating the infected bodily fluid sample with saponin and incubating the infected bodily fluid sample to allow for bacterial growth/expansion occur simultaneously or substantially simultaneously.

In an embodiment of any of the foregoing methods, the simultaneous or substantially simultaneous saponin lysis and incubation steps last for about 0.5 hours to about 5 hours.

In an embodiment of any of the foregoing methods, the simultaneous or substantially simultaneous saponin lysis and incubation steps last for about 0.5 hours to about 2 hours.

In an embodiment of any of the foregoing methods, the step of analyzing the multidimensional data further comprises the steps of:

i) calculating an adaptive, multidimensional Probability Binned-signature Quadratic Form (PB-sQF) statistical distance for each of the infected bodily fluid samples incubated with the at least one antibiotic and the paired control sample based on the results of the flow cytometry analysis;

ii) comparing the statistical distance from the patient's infected bodily fluid samples incubated with the at least one antibiotic to the paired control sample; and iii) determining whether the bacteria in the infected bodily fluid sample are susceptible to antibiotics or not (i.e., are antibiotic resistant).

In an embodiment of any of the foregoing methods, the step of determining antibiotic susceptibility lasts for about 0.5 hours to about 5 hours.

In an embodiment of any of the foregoing methods, the step of determining antibiotic susceptibility lasts for about 0.5 hours to about 2 hours.

In an embodiment of any of the foregoing methods, the method further comprises treating the subject based on the determination of antibiotic susceptibility.

In an embodiment of any of the foregoing methods, the method comprises treating the subject with a therapeutically effective amount of at least one antibiotic based on the determination of antibiotic susceptibility.

In another aspect, the present disclosure provides a method for treating a subject who has or is at risk for having bacteremia, the method comprising:

determining if the subject has bacteria in his bodily fluids that are susceptible to an antibiotic according to any of the methods according to any of the methods herein; and treating the subject based on the determination of antibiotic susceptibility.

In an embodiment, the method of treatment further comprises treating the subject with a therapeutically effective amount of at least one antibiotic based on the determination of susceptibility.

In another aspect, the present disclosure provides a method for treating bacteremia and/or preventing sepsis or other acute or systemic adverse immune responses in a subject who has or is at risk for having sepsis, the method comprising:

determining if the subject has bacteria in his bodily fluid that are susceptible to an antibiotic according to any of the methods according to any of the methods herein; and treating or preventing sepsis based on the determination of antibiotic susceptibility.

In an embodiment, the method further comprises treating bacteremia and/or preventing sepsis or other acute or systemic adverse immune responses by treating the subject with a therapeutically effective amount of at least one antibiotic based on the determination of susceptibility.

These and other objects, features and advantages of the present disclosure will become more apparent upon reading the following specification in conjunction with the accompanying description, claims and drawings.

BRIEF DESCRIPTION OF THE DRAWINGS

The accompanying Figures, which are incorporated in and constitute a part of this specification, illustrate several aspects described below, in accordance with some embodiments of the present disclosure.

(FIGS. 2A and 2B) Antibiotic induced scatter histograms (black contours) overlaid on paired no-antibiotic control (greyscale plot, lighter shades of grey indicating higher occurrence). BP: breakpoint. (FIG. 2A) Mu890 treated with tetracycline (Tet) at 1 µg/mL (MIC), gentamicin (Gen) at 8 µg/mL (MIC). and ampicillin (Amp) at 32 µg/mL (resistance breakpoint). (FIG. 2B) Mu14S treated with tetracycline at 16 µg/mL (resistance breakpoint), gentamicin at 8 µg/mL (MIC) and ampicillin at 32 µg/mL (resistance breakpoint). (FIG. 2C) PB-sQF distances for FIGS. 2A and 2B. The y-axis is the fold distance, (the test statistics normalized by the 99% confidence distance, beyond which samples are statistically different from the control). The 99% confidence fold-distance is represented by the thick black line equal to 1. Any test result exceeding the 99% confidence level (error bar included) is statistically different from the control and is an effective antibiotic treatment. Mu890 results: right. Mu14S results: left. Error bar is one standard deviation above and below the average fold distance obtained from triplicate trials. Details of test statistics and error bar calculation are presented in the Methods section herein.

FIGS. 4A-4C represent Mu890 recovered from human blood, diluted to 10% to approximate initial blood culture conditions. Complementary to FIGS. 2A-2C. (FIG. 4A) Tetracycline (FIG. 4B) Gentamicin (FIG. 4C) Ampicillin. FIGS. 4D-4F represent Mu890 pure culture started from around 1000 CFU/mL and incubated for 5 hours. (FIG. 4D) Tetracycline (FIG. 4E) Gentamicin (FIG. 4F) Ampicillin. Comparing the data with human blood (FIGS. 4A-4C) to the pure culture data (FIGS. 4D-4F), the bacteria signals appear at similar positions and disappeared at the same antibiotic concentration. In addition to the bacteria signals, the human blood data (FIGS. 4A-4C) also contain blood debris signals, appearing in the lower right corner. The blood debris signals are unchanged with different antibiotic treatments at different concentrations. The 1×MIC for tetracycline is 2 µg/mL and 8 µg/mL for gentamicin. For ampicillin, the resistant breakpoint for Enterobacteriaceae, 32 µg/mL, was used.

FIGS. 5A-5C represent Mu14S recovered from 10% human blood. Complementary to FIGS. 2A-2C. (FIG. 5A) Tetracycline (FIG. 5B) Gentamicin (FIG. 5C) Ampicillin. FIGS. 5D-5F represent Mu14S pure culture started from around 1000 CFU/mL and incubated for 5 hours. (FIG. 5D) Tetracycline (FIG. 5E) Gentamicin (FIG. 5F) Ampicillin. The 1×MIC for gentamicin is 8 µg/mL. For ampicillin and tetracycline, 32 µg/mL and 16 µg/mL were used. Both are the resistant breakpoint for Enterobacteriaceae.

(FIG. 6D) PB-sQF results for FIGS. 6A-6C). Because the fold distance (y-axis) is calculated by dividing the test statistic between the histogram for each dataset and its paired control, by the 99% confidence level distance, any distance (with error bars) encompassing or smaller than unity means that the corresponding conditions are not significantly different from the control. For each antibiotic, the resistant breakpoints of Enterobacteriaceae are 16 µg/mL for tetracycline and gentamicin and 32 µg/mL for ampicillin.

FIGS. 7A-7C represent Mu55 recovered from 10% human blood. Complementary to FIGS. 3A-3F. (FIG. 7A) Tetracycline (FIG. 7B) Gentamicin (FIG. 7C) Ampicillin. FIGS. 7D-7F represent Mu55 pure culture started from around 1000 CFU/mL and incubated for 5 hours. (FIG. 7D) Tetracycline (FIG. 7E) Gentamicin (FIG. 7F) Ampicillin. The 1×MIC for gentamicin is 1 µg/mL. For ampicillin and tetracycline, 32 µg/mL and 16 µg/mL were used. Both are the resistant breakpoint for Enterobacteriaceae.

FIGS. 8A-8C represent Mu670 recovered from 10% human blood. Complementary to FIGS. 3A-3F. (FIG. 8A) Tetracycline (FIG. 8B) Gentamicin (FIG. 8C) Ampicillin. FIGS. 8D-8F represent Mu670 pure culture started from around 1000 CFU/mL and incubated for 5 hours. (FIG. 8D) Tetracycline (FIG. 8E) Gentamicin (FIG. 8F) Ampicillin. The 1×MIC for tetracycline is 2 µg/mL and for gentamicin is 4 µg/mL. For ampicillin, the resistant breakpoint for Enterobacteriaceae, 32µg/mL, was used.

FIGS. 9A-9C represent M2 recovered from 10% human blood. Complementary to FIGS. 3A-3F. (FIG. 9A) Tetracycline (FIG. 9B) Gentamicin (FIG. 9C) Ampicillin. FIGS. 9D-9F represent M2 pure culture started from around 1000 CFU/mL and incubated for 5 hours. (FIG. 9D) Tetracycline (FIG. 9E) Gentamicin (FIG. 9F) Ampicillin. The 1×MIC for tetracycline is ¼ µg/mL and for gentamicin is 2 µg/mL. For ampicillin, the resistant breakpoint for penicillin-typed antibiotics for *Acinetobacter* spp., 128 µg/mL, was used.

(FIG. 10A) Blood only data. The black contour is the SST processed human blood after 4.5 hours of incubation. The greyscale plot is the unprocessed human blood. For FIGS. 10B-10C, the black contours are Flow cytometry data of (FIG. 10B) $10^6$ CFU/mL of *E. coli* spiked human blood (FIG. 10C) $10^7$ CFU/mL of *E. coli* spiked human blood. The greyscale plots are 10% human blood only. FSC: forward scatter. SSC: side scatter. (FIG. 10D) Cytometric data for IR786 fluorescence channel.

(FIG. 11B) *E. coli*. For both (FIG. 11A) and (FIG. 11B) the black contours were the 1% saponin-treated data while the greyscale plots were without saponin treatment. (FIG. 11C) MH-IR786 fluorescence signal in *E. coli* and blood. HB: human blood. BL: blank (no fluorescent MH-IR786 dye).

(FIG. 12B) 1000 CFU/mL *E. coli* spiked blood sample. The black contours are the penicillin g-treated data with the penicillin g concentration labeled on each figure. The greyscale plots are the no antibiotic controls. 1×MIC of penicillin g is 32 µg/mL for *E. coli* strain ATCC 33456. FSC: forward scatter. SSC: side scatter. (FIG. 12C) PB-sQF results for FIGS. 13A-13B and $10^5$ CFU/mL spiked blood sample.

(FIG. 13A) Lab strain ATCC 33456 is killed when introduced to human blood. (FIG. 13B) Clinical-isolate *E. coli* strain Mu14S exhibits some survival when added to human blood.

DETAILED DESCRIPTION OF THE DISCLOSURE

Figure 1:
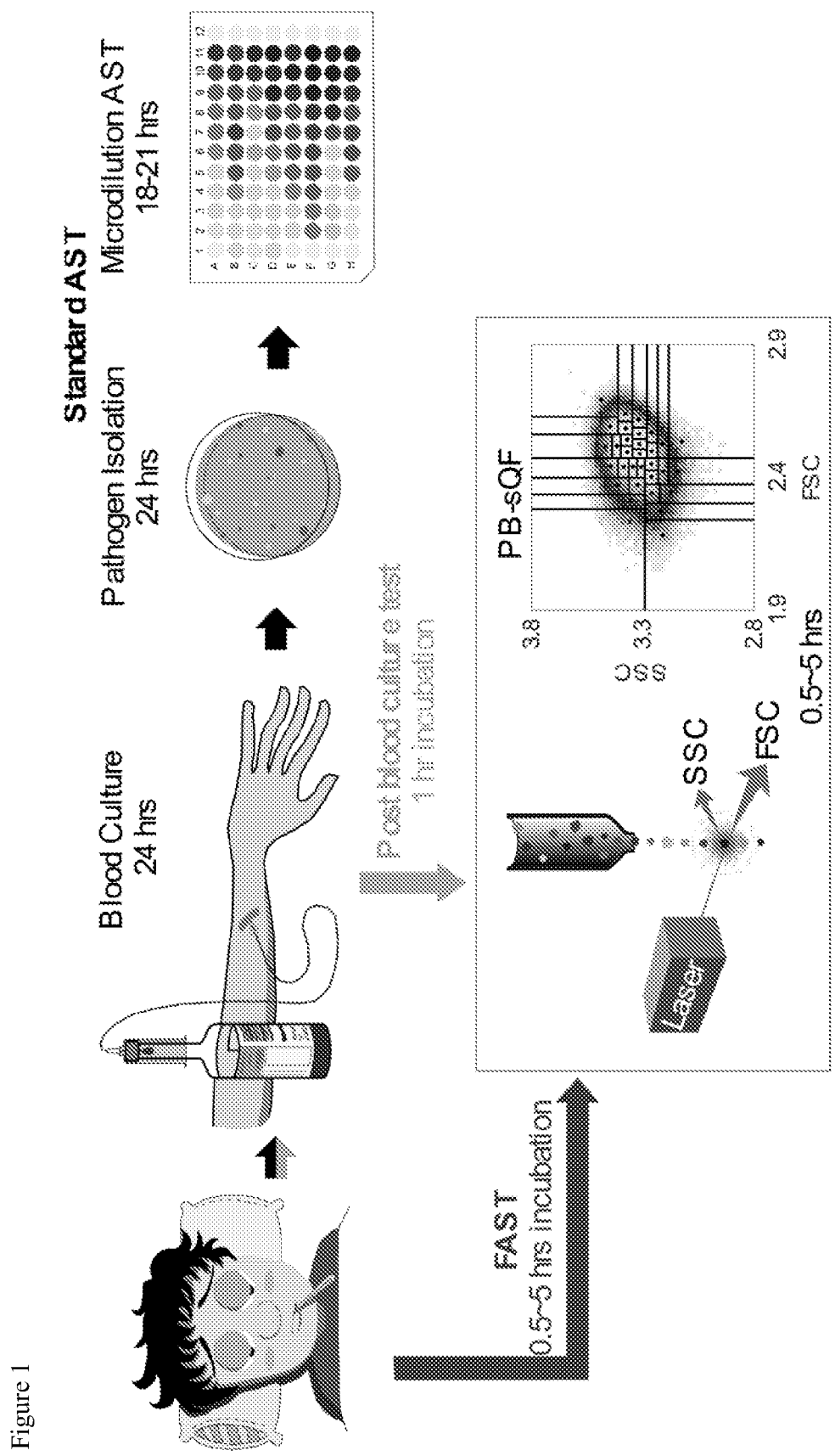
FIG. 1. Antibiotic susceptibility test (AST) timelines. (Top, black arrows) The standard clinical microbiology workflow requires >60 hours from initial sample collection. (light grey arrows) Timeline for the post-blood culture cytometric AST using PB-sQF distances[1] (dark gray arrow) Timeline from initial blood draw for Fast AST (i.e. FAST). FSC: forward scatter. SSC: side scatter. FSC: forward scatter. SSC: side scatter.

As specified in the Background Section, there is a great need in the art to identify technologies for rapid determination of antibiotic susceptibility of bacteria in patient bodily fluid samples and use this understanding to develop novel methods for such determinations, including methods that can accurately determine susceptibility for samples with high and low bacterial counts and can be completed within ten or fewer hours from initial sample collection. Blood is the most extreme example with extremely low CFU/mL leading to extreme immune responses, but rapid susceptibility determinations of low abundance bacteria, obscured by higher abundance mammalian cells in many other patient samples, such as sputum, urine, pus, saliva, cerebrospinal fluid, or other bodily fluids are also addressable with the methods described herein. The present disclosure satisfies this and other needs. Embodiments of the present disclosure relate generally to rapidly determining the antibiotic susceptibility of various bacteria in a patient bodily fluid sample (such as for example and not limitation, blood, sputum, pus, urine, plasma, serum, cerebrospinal fluid, and/or saliva). The method should take advantage of advanced detection methods such as flow cytometry (such as for example and not limitation, scattered light and/or fluorescence-based flow cytometric techniques), while improving assessment of samples with high bacterial counts (such as for example and not limitation, at least about 11,000 colony forming units (CFU) per mL bodily fluid to about 1,000,000 CFU/mL bodily fluid) and also with low bacterial counts (such as for example and not limitation, at least about 10 CFU/mL bodily fluid to about 10,000 CFU/mL bodily fluid), often in very high mammalian backgrounds, and be capable of completion within ten hours, preferably within eight hours, more preferably within five hours, and most preferably within three hours from initial sample collection. The method should provide improved susceptibility assessments based on use of statistical analyses or statistical distances including but not limited to adaptive, multidimensional Probability Binned-signature Quadratic Form (PB-sQF).

The inventors have developed a rapid, flow cytometry-based AST based on rigorous multidimensional statistical metrics[1] that matches the timescale of emerging post blood culture identification (~4 hrs).[8-10] The inventors' adaptive, multidimensional Probability Binned-signature Quadratic Form (PB-sQF) statistical distances[1] were shown to be ideal for quantifying small, but statistically significant changes relative to paired controls, even within broad, multidimensional flow cytometry datasets. PB-sQF was used to calculate the true linear distance between any two multidimensional histograms, thereby enabling rapid direct comparisons of changes within heterogeneous populations, relative to their paired controls. The inventors' prior order-of-magnitude improvement in post-blood culture time-to-result could, in most cases, be done label-free, and with bacteria-antibiotic combinations that had failed with previous cytometric tests.[1]

Taking blood infections as an example, without culture-based amplification, the highly disadvantageous bacteria: mammalian cell ratio, even in patients with bacteremia, generally requires that phenotypic ASTs remove nearly all mammalian cell background, without killing the bacteria. Additionally, sufficient bacteria must be recovered to allow assaying with multiple antibiotics at various concentrations, suggesting that at least some amplification, or a higher volume of blood (at ~100 CFU/mL), is needed. Because time is critical in ensuring appropriate treatment for patient survival[33] and reducing antibiotic resistance proliferation,[6] the invented method is capable of avoiding the need for lengthy culture-based amplification by utilizing saponin to complex with cholesterols and induce hemolysis,[34,35] without affecting bacterial growth or morphology.[36] This selective blood cell lysis enabled even very small numbers of bacteria to be directly collected from the blood and enriched in blood-free growth medium for cytometric detection. The inventors' use of robust statistics then enabled quantification of very few bacterial counts, such that much shorter growth and antibiotic sensitivity times can be achieved.

To facilitate an understanding of the principles and features of the various embodiments of the disclosure, various illustrative embodiments are explained below. Although exemplary embodiments of the disclosure are explained in detail, it is to be understood that other embodiments are contemplated. Accordingly, it is not intended that the disclosure is limited in its scope to the details of construction and arrangement of components set forth in the following description or examples. The disclosure is capable of other embodiments and of being practiced or carried out in various ways.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or," it may mean "exclusive-or," it may mean "one," it may mean "some, but not all," it may mean "neither," and/or it may mean "both." The term "or" is intended to mean an inclusive "or."

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present disclosure as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present disclosure are intended to be illustrative and not restrictive. Many suitable materials that would perform the same or a similar function as the materials described herein are intended to be embraced within the scope of the disclosure. Such other materials not described herein can include, but are not limited to, materials that are developed after the time of the development of the disclosure, for example. Any dimensions listed in the various drawings are for illustrative purposes only and are not intended to be limiting. Other dimensions and proportions are contemplated and intended to be included within the scope of the disclosure.

As used herein, the term "subject" or "patient" are used interchangeably and refer to mammals and include, without limitation, humans, companion animals and veterinary animals. In a preferred embodiment, the subject is human.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof, or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein the term "therapeutically effective" applied to dose or amount refers to that quantity of a compound or pharmaceutical composition that when administered to a subject for treating (e.g., preventing or ameliorating) a state, disorder or condition, is sufficient to cause such treatment. The "therapeutically effective amount" will vary depending on the compound or bacteria or analogues administered as well as the disease and its severity and the age, weight, physical condition and responsiveness of the mammal to be treated.

In accordance with the present disclosure there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning*

(1984); F. M. Ausubel et al. (eds.), *Current Protocols in Molecular Biology*, John Wiley & Sons, Inc. (1994); among others.

The present disclosure is directed to methods for (i) rapidly determining the antibiotic susceptibility of various bacteria in a subject's bodily fluid sample (preferably a blood sample), (ii) rapidly detecting the antibiotic susceptibility of bacteria in a subject's sample (preferably a blood sample), (iii) rapidly differentiating between the antibiotic susceptibilities of different bacteria in a subject's bodily fluid sample (preferably a blood sample), (iv) rapidly diagnosing a subject infected with antibiotic-susceptible bacteria or antibiotic-resistant bacteria in the subject (preferably in the subject's bloodstream); (v) rapidly classifying bacteria in a subject's bodily fluid sample (preferably a blood sample) as being susceptible to antibiotics or not susceptible to antibiotics (i.e., antibiotic resistant), (vi) treating the subject based on any of the foregoing methods and/or (vii) treating or preventing sepsis or other acute or systemic adverse immune responses in the subject based on any of the foregoing methods. In any of the foregoing methods, the patient's bodily fluid sample can be, for example and not limitation, blood, sputum, pus, urine, plasma, serum, cerebrospinal fluid, and/or saliva. The disclosed methods take advantage of advanced detection methods such as flow cytometry, measuring scattered light and/or fluorescence changes of multiple individual cells as reaction to antibiotic exposure, and can also improve assessment of samples with high bacterial counts (such as for example and not limitation, at least about 11,000 colony forming units (CFU) per mL bodily fluid to about 1,000,000 CFU/mL bodily fluid) and also with low bacterial counts (such as for example and not limitation, about 10 CFU/mL bodily fluid to about 10,000 CFU/mL bodily fluid). The disclosed methods can be completed within about ten hours, preferably within about eight hours, more preferably within about five hours, and most preferably within about three hours from initial sample collection. The present disclosure also provides improved susceptibility assessments based on use of statistics including for example and not limitation, adaptive, multidimensional Probability Binned-signature Quadratic Form (PB-sQF). Once the disclosed methods have identified the antibiotics to which the bacteria are susceptible, the subject can be treated with appropriate antibiotic therapy, such as for example and not limitation, therapeutically effective amounts of at least one antibiotic (or member of the same class of antibiotics, or an antibiotic with a similar mechanism of action) to which the bacteria are susceptible.

As discussed herein, the present disclosure can be carried out more rapidly than other methods of determining antibiotic susceptibility. The described methods may take at least about 0.5 hours to about ten hours, at least about 0.5 hours to about nine hours, at least about 0.5 hours to about eight hours, at least about 0.5 hours to about seven hours, at least about 0.5 hours to about six hours, at least about 0.5 hours to about five hours, at least about 0.5 hours to about four hours, at least about 0.5 hours to about three hours, at least about 0.5 hours to about two hours, and/or at least about 0.5 hours to about one hour, including all time points therebetween.

The present disclosure includes the use of saponin to lyse the eukaryotic (e.g., mammalian) cells present in the sample. The inventors surprisingly found that saponin can be used to recover bacteria from the bodily fluid sample prior to culture-based amplification, and can be useful with bodily fluid samples with low bacterial counts. In the present disclosure, the methods involved diluting the bodily fluid sample, lysing the bodily fluid directly with saponin to recover the very low counts of bacteria, then amplifying the bacteria via culture-based expansion, if needed. In other words, any use of saponin in the present disclosure occurred before the culture-based expansion is begun to recover low counts of bacteria from the diluted infected bodily fluid sample. Prior methods of saponin lysis occur after a positive blood culture. Without wishing to be bound by theory, it is suggested that the saponin lysis prior to culture-based amplification enables much faster ASTs (antimicrobial susceptibility tests) by selective removal of mammalian cell background, and that such step can be useful with samples with low bacterial counts. The duration of the saponin lysis step was also determined to be important in obtaining a sample with lysed eukaryotic (e.g., mammalian) cells but intact bacteria, as discussed in more detail herein.

The present disclosure enables methods of determining antibiotic susceptibility using bodily fluid samples from a subject (such as for example and not limitation, blood, sputum, pus, urine, plasma, serum, cerebrospinal fluid, and/or saliva, and preferably blood) that are diluted for further analysis. For example, the bodily fluid sample may be diluted to any amount between about 1% of the initial sample volume to about 99% of the initial sample volume (inclusive of all percentages therebetween), with the diluent being a growth medium for bacteria. The growth medium may be optimized for gram positive and/or gram negative bacteria. During standard blood culturing, for example, some amount of the subject's blood sample is generally diluted into a high growth medium to promote bacterial growth.

The methods described herein in some embodiments are capable of determining antibiotic susceptibility in bodily fluid samples that have high bacterial counts, such as for example and not limitation, urine, pus, sputum, and cerebrospinal fluid. The methods described herein in some embodiments are capable of determining antibiotic susceptibility in bodily fluid samples comprising about 11,000 CFU/mL bodily fluid to about 1,000,000 CFU/mL bodily fluid, about 11,000 CFU/mL bodily fluid to about 500,000 CFU/mL bodily fluid, about 11,000 CFU/mL bodily fluid to about 250,000 CFU/mL bodily fluid, about 11,000 CFU/mL bodily fluid to about 100,000 CFU/mL bodily fluid, about 11,000 CFU/mL bodily fluid to about 50,000 CFU/mL bodily fluid, about 11,000 CFU/mL bodily fluid to about 25,000 CFU/mL bodily fluid, and about 11,000 CFU/mL bodily fluid to about 20,000 CFU/mL bodily fluid. In methods comprising the use of bodily fluid samples with high bacterial counts and low eukaryotic (e.g., mammalian) cell counts, such as for example and not limitation, urine, pus, and cerebrospinal samples, it may be possible to omit one or more steps that enrich the bacterial count of the sample, including diluting the bodily fluid sample with growth medium, and/or treating the diluted bodily fluid sample with saponin to lyse the eukaryotic (e.g., mammalian) cells, and/or incubating the diluted bodily fluid sample to allow bacterial growth. For example and not limitation, in the case of a urine sample, it may be desirable to omit all three steps, or to omit two steps, or to omit one step, depending on the bacterial count in the sample, in order to carry out the described methods (e.g., it may be desirable to isolate the urine sample and then proceed directly to preparing the sample for flow cytometric analysis). In methods comprising the use of bodily fluid samples with both high bacterial counts and high eukaryotic (e.g., mammalian) cell counts, such as for example and not limitation, sputum, it may be possible to omit one or more steps that enrich the bacterial count of the sample, including diluting the bodily fluid sample with growth medium, and/or treating the diluted bodily fluid sample with saponin to lyse the eukaryotic (e.g., mammalian) cells, and/or incubating the diluted bodily fluid sample to allow bacterial growth. For example and not limitation, in the case of a sputum sample, it may be desirable to omit all three steps, or to omit two steps, or to omit one step, depending on the bacterial count in the sample, in order to carry out the described methods (e.g., it may be desirable to treat the sputum sample with saponin to lyse the mammalian cells but not to dilute it with growth medium or incubate it to allow for bacterial growth).

In one aspect, the present disclosure provides a method for rapidly determining the antibiotic susceptibility of various bacteria in a subject's bodily fluid sample, the method comprising:
    a) isolating the infected bodily fluid sample from the subject;
    b) optionally diluting the infected bodily fluid sample with a bacterial growth medium;
    c) optionally treating the infected bodily fluid sample with saponin;
    d) optionally incubating the infected bodily fluid sample to allow for bacterial growth;
    e) dividing the infected bodily fluid sample into samples for incubation with at least one antibiotic and a paired control sample that is not incubated with any antibiotic;
    f) collecting multidimensional data via flow cytometry of the infected bodily fluid samples incubated with the at least one antibiotic and the paired control sample; and
    (g) analyzing the multidimensional data to determine if the bacteria are susceptible to any of the at least one antibiotics.

In another aspect, the present disclosure provides a method for rapidly detecting the antibiotic susceptibility of bacteria in a subject's bodily fluid sample, the method comprising:
    a) isolating the infected bodily fluid sample from the subject;
    b) optionally diluting the infected bodily fluid sample with a bacterial growth medium;
    c) optionally treating the infected bodily fluid sample with saponin;
    d) optionally incubating the infected bodily fluid sample to allow for bacterial growth;
    e) dividing the infected bodily fluid sample into samples for incubation with at least one antibiotic and a paired control sample that is not incubated with any antibiotic;
    f) collecting multidimensional data via flow cytometry of the infected bodily fluid samples incubated with the at least one antibiotic and the paired control sample; and
    (g) analyzing the multidimensional data to determine if the bacteria are susceptible to any of the at least one antibiotics.

In another aspect, the present disclosure provides a method for rapidly differentiating between the antibiotic susceptibilities of different bacteria in a subject's bodily fluid sample, the method comprising:
    a) isolating the infected bodily fluid sample from the subject;
    b) optionally diluting the infected bodily fluid sample with a bacterial growth medium;
    c) optionally treating the infected bodily fluid sample with saponin;
    d) optionally incubating the infected bodily fluid sample to allow for bacterial growth;
    e) dividing the infected bodily fluid sample into samples for incubation with at least one antibiotic and a paired control sample that is not incubated with any antibiotic;
    f) collecting multidimensional data via flow cytometry of the infected bodily fluid samples incubated with the at least one antibiotic and the paired control sample; and
    (g) analyzing the multidimensional data to determine if the bacteria are susceptible to any of the at least one antibiotics.

In another aspect, the present disclosure provides a method for rapidly diagnosing a subject with antibiotic-susceptible bacteria or antibiotic-resistant bacteria in the subject's bodily fluids, the method comprising:
    a) isolating the infected bodily fluid sample from the subject;
    b) optionally diluting the infected bodily fluid sample with a bacterial growth medium;
    c) optionally treating the infected bodily fluid sample with saponin;
    d) incubating the infected bodily fluid sample to allow for bacterial growth;
    e) dividing the infected bodily fluid sample into samples for incubation with at least one antibiotic and a paired control sample that is not incubated with any antibiotic;
    f) collecting multidimensional data via flow cytometry of the infected bodily fluid samples incubated with the at least one antibiotic and the paired control sample; and
    (g) analyzing the multidimensional data to determine if the bacteria are susceptible to any of the at least one antibiotics.

In another aspect, the present disclosure provides a method for rapidly classifying bacteria in a subject's bodily fluid sample as being susceptible to antibiotics or not susceptible to antibiotics (i.e., antibiotic resistant), the method comprising:
    a) isolating the infected bodily fluid sample from the subject;
    b) optionally diluting the infected bodily fluid sample with a bacterial growth medium;
    c) optionally treating the infected bodily fluid sample with saponin;
    d) optionally incubating the infected bodily fluid sample to allow for bacterial growth;
    e) dividing the infected bodily fluid sample into samples for incubation with at least one antibiotic and a paired control sample that is not incubated with any antibiotic;
    f) collecting multidimensional data via flow cytometry of the infected bodily fluid samples incubated with the at least one antibiotic and the paired control sample; and
    (g) analyzing the multidimensional data to determine if the bacteria are susceptible to any of the at least one antibiotics.

The present disclosure also enables methods of determining antibiotic susceptibility in bodily fluid samples that have low bacterial counts, such as for example and not limitation, blood or blood-based samples. The methods described herein in some embodiments are capable of determining antibiotic susceptibility in bodily fluid samples comprising about 10 CFU/mL bodily fluid to about 10,000 CFU/mL bodily fluid, 10 CFU/mL bodily fluid to about 3,000 CFU/mL bodily fluid, about 10 CFU/mL bodily fluid to about 2,000 CFU/mL bodily fluid, about 10 CFU/mL bodily fluid to about 1,000 CFU/mL bodily fluid, about 10 CFU/mL bodily fluid to about 500 CFU/mL bodily fluid, about 10 CFU/mL bodily fluid to about 300 CFU/mL bodily fluid, about 10 CFU/mL bodily fluid to about 100 CFU/mL bodily fluid, about 10 CFU/mL bodily fluid to about 50 CFU/mL bodily fluid, about 10 CFU/mL bodily fluid to about 40 CFU/mL bodily fluid, about 10 CFU/mL bodily fluid to about 30 CFU/mL bodily fluid, and about 10 CFU/mL bodily fluid to about 20 CFU/mL bodily fluid. In instances in which the samples have low bacterial counts, it may be advisable to include one or more steps that enrich the bacterial count of the sample, including diluting the bodily fluid sample with growth medium, and/or treating the diluted bodily fluid sample with saponin to lyse the eukaryotic (e.g., mammalian) cells, and/or incubating the diluted bodily fluid sample to allow bacterial growth. For example and not limitation, in the case of a blood sample, it may be desirable to include all three steps, or to include two steps, or to include one step, depending on the bacterial count in the sample, in order to carry out the described methods (e.g., it may be desirable to dilute the blood sample with growth medium, to then treat the diluted blood sample with saponin, and then to incubate the diluted blood sample to allow for bacterial growth).

In one aspect, the present disclosure provides a method for rapidly determining the antibiotic susceptibility of various bacteria in a subject's bodily fluid sample, the method comprising:

a) isolating the infected bodily fluid sample from the subject;
b) diluting the infected bodily fluid sample with a bacterial growth medium;
c) treating the diluted infected bodily fluid sample with saponin;
d) incubating the diluted infected bodily fluid sample to allow for bacterial growth;
e) dividing the diluted infected bodily fluid sample into samples for incubation with at least one antibiotic and a paired control sample that is not incubated with any antibiotic;
f) collecting multidimensional data via flow cytometry of the diluted infected bodily fluid samples incubated with the at least one antibiotic and the paired control sample; and
(g) analyzing the multidimensional data to determine if the bacteria are susceptible to any of the at least one antibiotics.

In another aspect, the present disclosure provides a method for rapidly detecting the antibiotic susceptibility of bacteria in a subject's bodily fluid sample, the method comprising:

a) isolating the infected bodily fluid sample from the subject;
b) diluting the infected bodily fluid sample with a bacterial growth medium;
c) treating the diluted infected bodily fluid sample with saponin;
d) incubating the diluted infected bodily fluid sample to allow for bacterial growth;
e) dividing the diluted infected bodily fluid sample into samples for incubation with at least one antibiotic and a paired control sample that is not incubated with any antibiotic;
f) collecting multidimensional data via flow cytometry of the diluted infected bodily fluid samples incubated with the at least one antibiotic and the paired control sample; and
(g) analyzing the multidimensional data to determine if the bacteria are susceptible to any of the at least one antibiotics.

In another aspect, the present disclosure provides a method for rapidly differentiating between the antibiotic susceptibilities of different bacteria in a subject's bodily fluid sample, the method comprising:

a) isolating the infected bodily fluid sample from the subject;
b) diluting the infected bodily fluid sample with a bacterial growth medium;
c) treating the diluted infected bodily fluid sample with saponin;
d) incubating the diluted infected bodily fluid sample to allow for bacterial growth;
e) dividing the diluted infected bodily fluid sample into samples for incubation with at least one antibiotic and a paired control sample that is not incubated with any antibiotic;
f) collecting multidimensional data via flow cytometry of the diluted infected bodily fluid samples incubated with the at least one antibiotic and the paired control sample; and
(g) analyzing the multidimensional data to determine if the bacteria are susceptible to any of the at least one antibiotics.

In another aspect, the present disclosure provides a method for rapidly diagnosing a subject with antibiotic-susceptible bacteria or antibiotic-resistant bacteria in the subject's bodily fluids, the method comprising:

a) isolating the infected bodily fluid sample from the subject;
b) diluting the infected bodily fluid sample with a bacterial growth medium;
c) treating the diluted infected bodily fluid sample with saponin;
d) incubating the diluted infected bodily fluid sample to allow for bacterial growth;
e) dividing the diluted infected bodily fluid sample into samples for incubation with at least one antibiotic and a paired control sample that is not incubated with any antibiotic;
f) collecting multidimensional data via flow cytometry of the diluted infected bodily fluid samples incubated with the at least one antibiotic and the paired control sample; and
(g) analyzing the multidimensional data to determine if the bacteria are susceptible to any of the at least one antibiotics.

In another aspect, the present disclosure provides a method for rapidly classifying bacteria in a subject's bodily fluid sample as being susceptible to antibiotics or not susceptible to antibiotics (i.e., antibiotic resistant), the method comprising:

a) isolating the infected bodily fluid sample from the subject;
b) diluting the infected bodily fluid sample with a bacterial growth medium;
c) treating the diluted infected bodily fluid sample with saponin;
d) incubating the diluted infected bodily fluid sample to allow for bacterial growth;
e) dividing the diluted infected bodily fluid sample into samples for incubation with at least one antibiotic and a paired control sample that is not incubated with any antibiotic;
f) collecting multidimensional data via flow cytometry of the diluted infected bodily fluid samples incubated with the at least one antibiotic and the paired control sample; and
(g) analyzing the multidimensional data to determine if the bacteria are susceptible to any of the at least one antibiotics.

In an embodiment of any of the foregoing methods, the bodily fluid sample is about 0.01 mL to about 0.5 mL, preferably about 0.05 to about 0.5 mL.

In an embodiment of any of the foregoing method, the step of treating the diluted bodily fluid sample with saponin occurs at a temperature between 25° C. and 37° C. inclusive.

In an embodiment of any of the foregoing methods, the steps of treating the diluted bodily fluid sample with saponin and incubating the diluted bodily fluid sample to allow for bacterial growth occur simultaneously. In an embodiment of any of the foregoing methods, the steps of treating the diluted bodily fluid sample with saponin and incubating the diluted bodily fluid sample to allow for bacterial growth occur substantially simultaneously.

In an embodiment of any of the foregoing methods, the steps of treating the diluted bodily fluid sample with saponin and incubating the diluted bodily fluid sample to allow for bacterial growth occur at a temperature between 20° C. and 42° C., preferably between 25° C. and 37° C.

In an embodiment of any of the foregoing methods, the step of treating the diluted bodily fluid sample with saponin is at least about 5 minutes. In an embodiment of any of the foregoing methods, the step of treating the diluted bodily fluid sample with saponin is at least about 10 minutes. In an embodiment of any of the foregoing methods, the step of treating the diluted bodily fluid sample with saponin is at least about 15 minutes. In an embodiment of any of the foregoing methods, the step of treating the diluted bodily fluid sample with saponin is at least about 20 minutes. In an embodiment of any of the foregoing methods, the step of treating the diluted bodily fluid sample with saponin is at most about 45 minutes. In an embodiment of any of the foregoing methods, the step of treating the diluted bodily fluid sample with saponin is at most about 30 minutes.

In an embodiment of any of the foregoing methods, the steps of treating the diluted bodily fluid sample with saponin and incubating the diluted bodily fluid sample to allow for bacterial growth/expansion occur simultaneously or substantially simultaneously. In a further embodiment, such simultaneous or substantially simultaneous saponin lysis and incubation steps last for about 0.5 hours to about 5 hours, about 0.5 hours to about 4.5 hours, about 0.5 hours to about 4 hours, about 0.5 hours to about 3.5 hours, about 0.5 hours to about 3 hours, about 0.5 hours to about 2.5 hours, about 0.5 hours to about 2 hours, about 0.5 hours to about 1.5 hours, and/or about 0.5 hours to about 1 hour. Preferably, the simultaneous or substantially simultaneous saponin lysis and incubation steps last for about 0.5 hours to about 2 hours.

In an embodiment of any of the foregoing methods, the method may also include an additional step to remove eukaryotic (e.g., mammalian) cells, such as for example and not limitation, size-based filtration, size-exclusion chromatography, and/or centrifugation.

In an embodiment of any of the foregoing methods, the step of analyzing the multidimensional data further comprises the steps of:

i) calculating an adaptive, multidimensional Probability Binned-signature Quadratic Form (PB-sQF) statistical distance for each of the diluted infected bodily fluid samples incubated with the at least one antibiotic and the paired control sample based on the results of the flow cytometry analysis;

ii) comparing the statistical distance from the patient's diluted infected bodily fluid samples incubated with the at least one antibiotic to the paired control sample; and iii) determining whether the bacteria in the diluted infected bodily fluid sample are susceptible to antibiotics or not (i.e., are antibiotic resistant).

In an embodiment of any of the foregoing methods, steps e) through g) lasts for about 0.5 hours to about 5 hours, about 0.5 hours to about 4.5 hours, about 0.5 hours to about 4 hours, about 0.5 hours to about 3.5 hours, about 0.5 hours to about 3 hours, about 0.5 hours to about 2.5 hours, about 0.5 hours to about 2 hours, about 0.5 hours to about 1.5 hours, and/or about 0.5 hours to about 1 hour. Preferably, the step of determining antibiotic susceptibility lasts for about 0.5 hours to about 2 hours.

In an embodiment of any of the foregoing methods, the method further comprises treating the subject based on the determination of antibiotic susceptibility. In a further embodiment, the method comprises treating the subject with a therapeutically effective amount of at least one antibiotic based on the determination of antibiotic susceptibility. In some embodiments, the antibiotic used may be in the same class of antibiotic as the antibiotic used in the assay (such as for example and not limitation, a beta-lactam, a penicillin, a cephalosporin, a macrolide, a fluoroquinolone, a tetracycline, a monobactam, a carbapenem, and/or an aminoglycoside). In other embodiments, the antibiotic used may have the same mechanism of as the antibiotic used in the assay (such as for example and not limitation, an inhibitor of cell wall synthesis, an inhibitor of protein synthesis, an inhibitor of DNA synthesis, an inhibitor of RNA synthesis, an inhibitor of mycolic acid synthesis, and/or an inhibitor of folic acid synthesis).

In a related aspect, the present disclosure provides a method for treating the subject based on any of the methods described herein. In an embodiment, the method of treatment comprises treating the subject with a therapeutically effective amount of at least one antibiotic based on the determination of susceptibility. In some embodiments, the antibiotic used may be in the same class of antibiotic as the antibiotic used in the assay (such as for example and not limitation, a beta-lactam, a penicillin, a cephalosporin, a macrolide, a fluoroquinolone, a tetracycline, a monobactam, a carbapenem, and/or an aminoglycoside). In other embodiments, the antibiotic used may have the same mechanism of as the antibiotic used in the assay (such as for example and not limitation, an inhibitor of cell wall synthesis, an inhibitor of protein synthesis, an inhibitor of DNA synthesis, an inhibitor of RNA synthesis, an inhibitor of mycolic acid synthesis, and/or an inhibitor of folic acid synthesis).

In a related aspect, the present disclosure provides a method for treating bacteremia and/or preventing sepsis or other acute or systemic adverse immune responses in the subject based on any of the methods described herein. In an embodiment, the method of treating or preventing sepsis comprises treating the subject with a therapeutically effective amount of at least one antibiotic based on the determination of susceptibility. In some embodiments, the antibiotic used may be in the same class of antibiotic as the antibiotic used in the assay (such as for example and not limitation, a beta-lactam, a penicillin, a cephalosporin, a macrolide, a fluoroquinolone, a tetracycline, a monobactam, a carbapenem, and/or an aminoglycoside). In other embodiments, the antibiotic used may have the same mechanism of as the antibiotic used in the assay (such as for example and not limitation, an inhibitor of cell wall synthesis, an inhibitor of protein synthesis, an inhibitor of DNA synthesis, an inhibitor of RNA synthesis, an inhibitor of mycolic acid synthesis, and/or an inhibitor of folic acid synthesis).

In a related aspect, the present disclosure provides a method for treating and/or preventing an infection (such as for example and not limitation, urinary tract infections, diabetic lesions, upper and/or lower respiratory infections, localized infections, and/or meningitis) in the subject based on any of the methods described herein. In an embodiment, the method of treating or preventing sepsis comprises treating the subject with a therapeutically effective amount of at least one antibiotic based on the determination of susceptibility. In some embodiments, the antibiotic used may be in the same class of antibiotic as the antibiotic used in the assay (such as for example and not limitation, a beta-lactam, a penicillin, a cephalosporin, a macrolide, a fluoroquinolone, a tetracycline, a monobactam, a carbapenem, and/or an aminoglycoside). In other embodiments, the antibiotic used may have the same mechanism of as the antibiotic used in the assay (such as for example and not limitation, an inhibitor of cell wall synthesis, an inhibitor of protein synthesis, an inhibitor of DNA synthesis, an inhibitor of RNA synthesis, an inhibitor of mycolic acid synthesis, and/or an inhibitor of folic acid synthesis).

EXAMPLES

The present disclosure is also described and demonstrated by way of the following examples. However, the use of these and other examples anywhere in the specification is illustrative only and in no way limits the scope and meaning of the disclosure or of any exemplified term. Likewise, the disclosure is not limited to any particular preferred embodiments described here. Indeed, many modifications and variations of the disclosure may be apparent to those skilled in the art upon reading this specification, and such variations can be made without departing from the disclosure in spirit or in scope. The disclosure is therefore to be limited only by the terms of the appended claims along with the full scope of equivalents to which those claims are entitled.

Example 1. Development of the FAST Assay

Herein is described a rapid, flow cytometry-based AST based on rigorous multidimensional statistical metrics[1] that matches the timescale of emerging post blood culture identification (~4 hrs).[8-10] The inventors' adaptive, multidimensional Probability Binned-signature Quadratic Form (PB-sQF) statistical distances[1] were shown to be ideal for quantifying small, but statistically significant changes relative to paired controls, even within broad, multidimensional flow cytometry datasets. PB-sQF was used to calculate the true linear distance between any two multidimensional histograms, thereby enabling rapid direct comparisons of changes within heterogeneous populations, relative to their paired controls. The inventors' prior order-of-magnitude improvement in post-blood culture time-to-result could, in most cases, be done label-free, and with bacteria-antibiotic combinations that had failed with previous cytometric tests.[1]

Without blood culture-based amplification, the highly disadvantageous bacteria:mammalian cell ratio, even in patients with bacteremia, generally requires that phenotypic ASTs remove nearly all mammalian cell background, without killing the bacteria. Additionally, sufficient bacteria must be recovered to allow assaying with multiple antibiotics at various concentrations, suggesting that at least some amplification, or a higher volume of blood (at ~100 CFU/mL), is needed. Because time is critical in ensuring appropriate treatment for patient survival[33] and reducing antibiotic resistance proliferation,[6] the invented method is capable of avoiding the need for lengthy blood culture by utilizing saponin to complex with cholesterols and induce hemolysis,[34,35] without affecting bacterial growth or morphology.[36] This selective blood cell lysis enabled even very small numbers of bacteria to be directly collected from the blood and enriched in blood-free growth medium for cytometric detection. The inventors' use of robust statistics then enabled quantification of very few bacterial counts, such that much shorter growth and antibiotic sensitivity times can be achieved.

Results To demonstrate acceleration of the timeline for the inventive Fast AST (i.e., FAST, depicted in FIG. 1), the inventors obtained multidrug resistant, blood isolates of common bacteremia-causing pathogens (*E. coli*, *K. pneumoniae*, and *A. nosocomialis*). Varied counts of bacteria were mixed with human blood and diluted 1:9 (v/v) with bacterial growth medium to desired bacterial concentrations (<10 CFU/mL final solution) and plated to independently confirm CFU/mL blood. Saponin was immediately added and the samples shaken for 15 minutes to achieve selective blood cell lysis. After hemolysis, bacteria were spun down and washed with PBS. The pellets were resuspended in bacterial growth medium and incubated at 37° C. for 2 hours, followed by another 3-hour incubation with antibiotics at various fractions of the minimum inhibition concentration (MIC, as independently determined by microdilution from the pure starting culture, Table 1) for sensitive strains or at the CLSI MIC resistant breakpoints[12] for the highly resistant strains. Changes in scattered light signals largely resulting from bacterial growth inhibition were monitored by flow cytometry, and the difference in the 2-D scatter histograms with and without antibiotic treatment was quantified with PB-sQF statistics.[1] Using PB-sQF, distance was calculated for each antibiotic concentration relative to its own no-antibiotic control and expressed as "fold distance" relative to the 99% confidence limit distance between the no-antibiotic control and the sensitive breakpoint. This allowed comparison of fold distances among all samples as each is individually paired to its own control, as is each replicate.

More detailed procedures are given in Materials and Methods section herein.

TABLE 1

MIC (μg/mL) for each antibiotic/bacteria combination.

| MIC (S/I/R) | *E. coli* Mu14S | *E. coli* Mu890 | *K. pneumoniae* Mu670 | *K. pneumoniae* Mu55 | *A. nosocomialis* M2 |
|---|---|---|---|---|---|
| Tetracycline | >64 (R) | 1 (S) | 2 (S) | >64 (R) | 1 (S) |
| Gentamicin | 8 (I) | 8 (I) | 4 (S) | 1 (S) | 2 (S) |
| Ampicillin | >1024 (R) | >1024 (R) | >1024 (R) | >1024 (R) | >1024 (R) |

The MICs were determined from microdilution AST. S, I, and R represent sensitive, intermediate and resistant according to the 2016 Clinical & Laboratory Standards Institute (CLSI) handbook.[12]

Multidrug-resistant *E. coli* isolates.

Two Multidrug-Resistant *E. coli* Clinical Isolates were Tested, Mu890 and Mu14S.

Figures 2A, 2B, 2C:
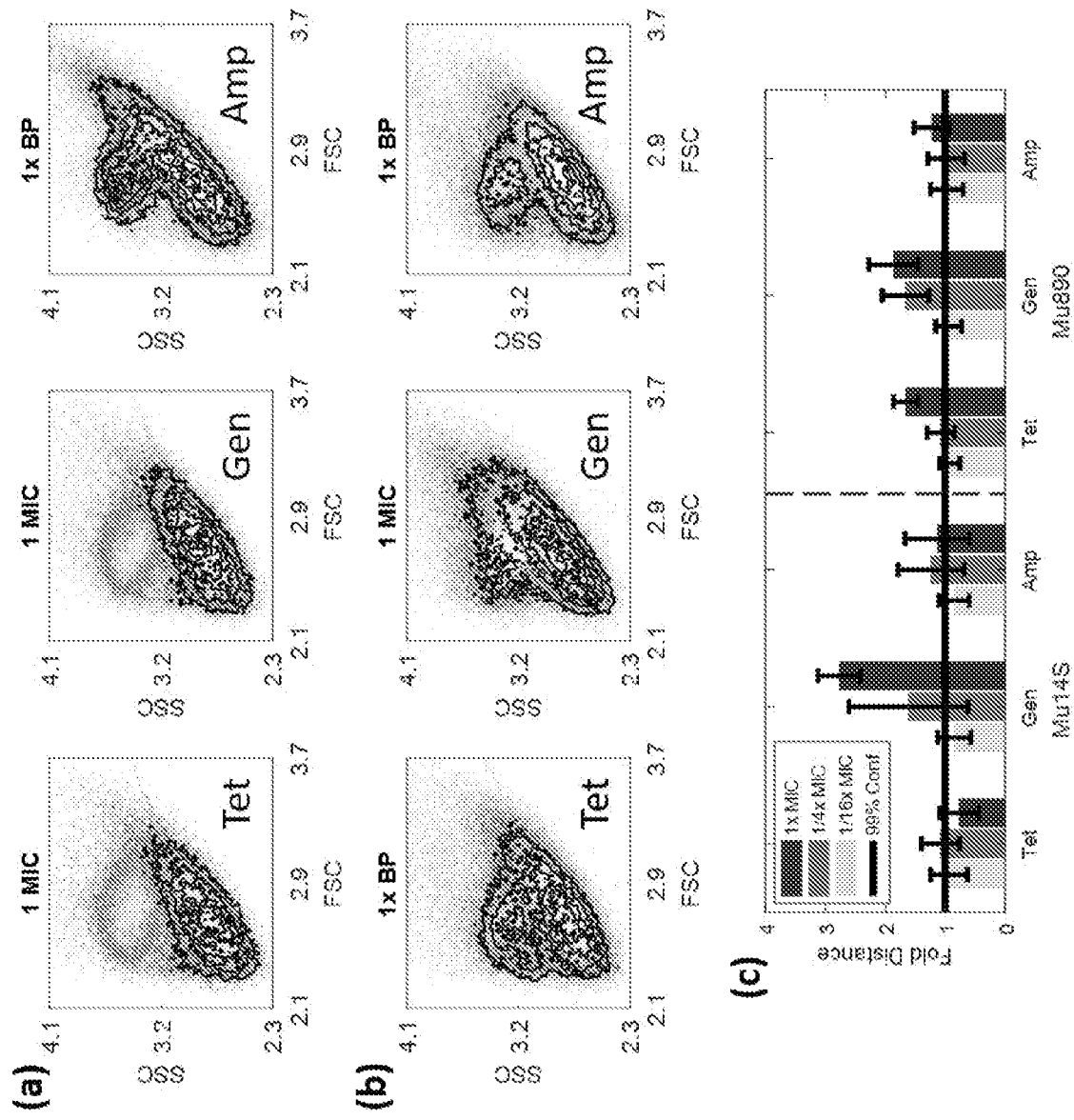
FIGS. 2A-2C. FAST antibiotic-induced scatter signals for *E. coli* isolates Mu890 and Mu14S.

Following the hemolysis and growth procedure outlined above, flow cytometry was used to collect forward and side scattered light signals. Statistical comparison of these histograms (FIGS. 2A-2C) demonstrates that susceptibility testing is readily performed by immediate hemolysis of 0.5 mL blood, followed by 2-hrs pre-incubation, and 3-hrs AST. When treated at the MICs of tetracycline or gentamicin, to which Mu890 is sensitive and intermediate, respectively, the Mu890 signals disappeared, indicating effective growth inhibition (FIG. 2A). When treated with 32 µg/mL ampicillin (the Enterobacteriaceae resistance breakpoint), however, scatter signals were indistinguishable from those of the no-antibiotic control (FIG. 2A). The complete cytometric data over 16-fold ranges encompassing the sensitive to resistant breakpoints of ineffective antibiotics or from $\frac{1}{16}\times$ MIC to 1×MIC for antibiotics to which Mu890 are sensitive are in FIGS. 4A-4F. PB-sQF fold distance-based FAST beyond the 99% confidence levels match the much slower microscan AST data, demonstrating that tetracycline and gentamicin are indeed effective for Mu890 (FIG. 2C). The actual starting CFU/mL of Mu890 were confirmed with overnight plating to be 3, 3, and 5 CFU/mL for tetracycline, gentamicin, and ampicillin experiments, respectively. Since the *E. coli*/human blood was diluted 10-fold, the real concentrations before dilution corresponded to ~30, 30 and 50 CFU/mL of whole blood.

Figures 6A, 6B, 6C, 6D:
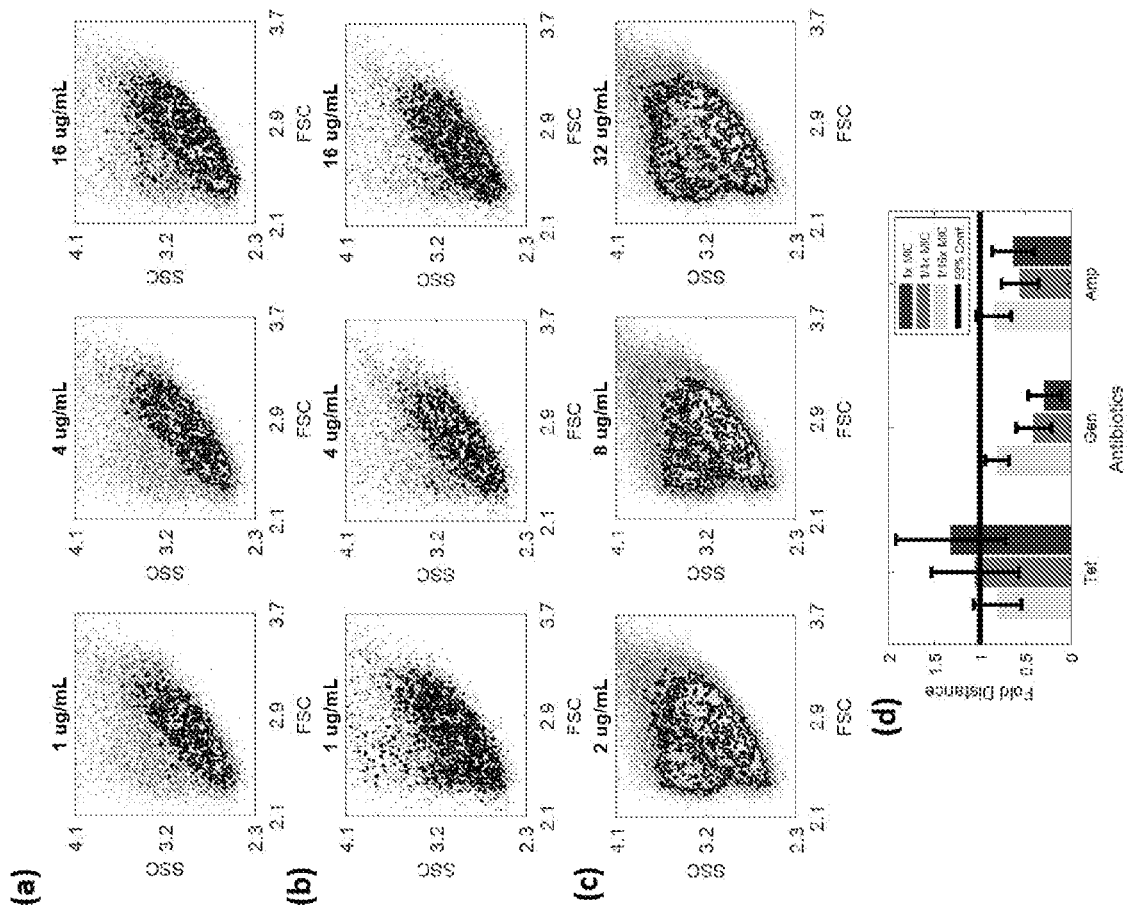
FIGS. 6A-6D. Antibiotic-treated 10% human blood only results. Cytometric data with (FIG. 6A) Ampicillin (FIG. 6B) Tetracycline (FIG. 6C) Gentamicin. The greyscale plots are the no-antibiotic controls and the black contour plots are the antibiotic-treated data with the antibiotic concentration indicated at each plot.
Figures 7A, 7B, 7C, 7D, 7E, 7F:
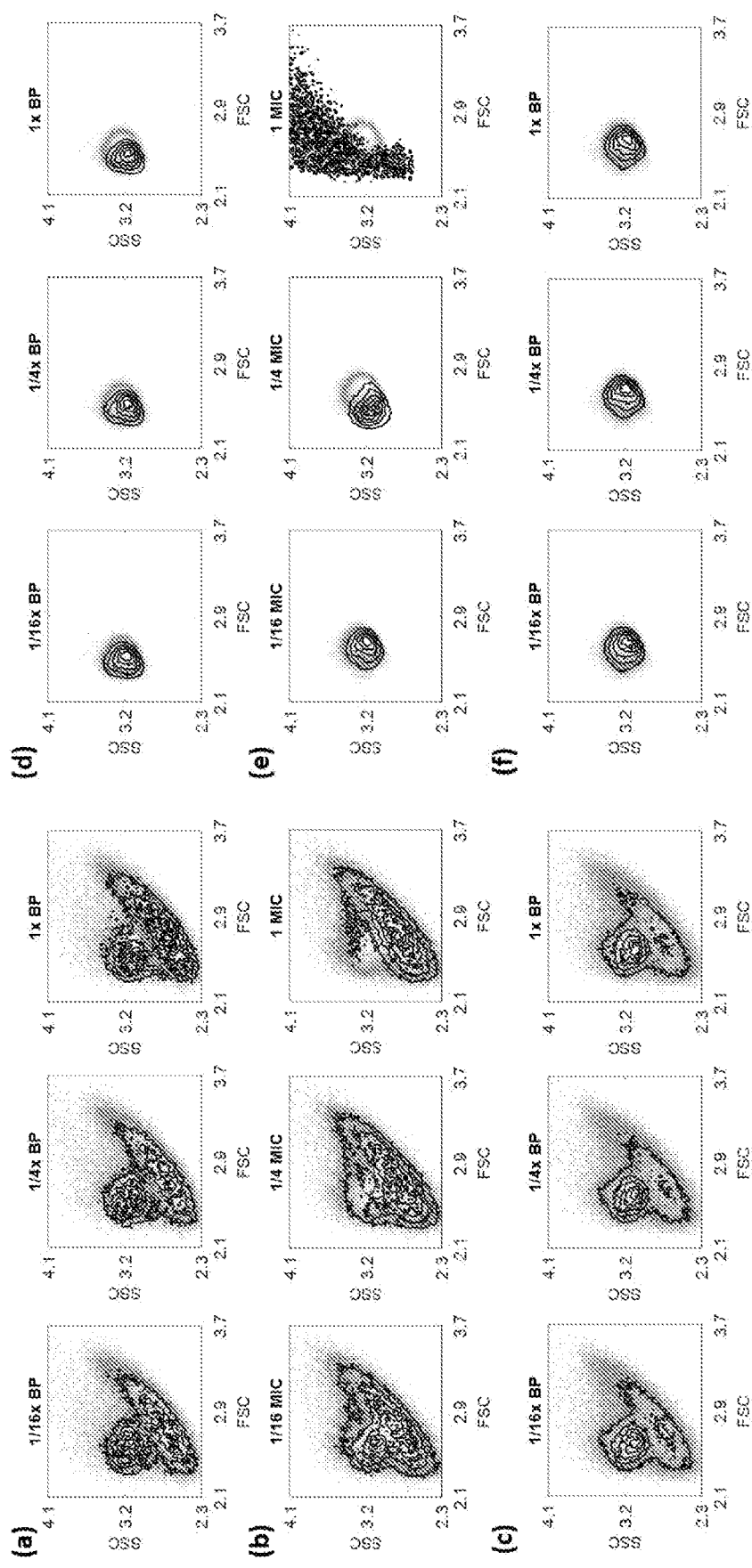
FIGS. 7A-7F. Bactericidal Antibiotic-induced scatter changes for *K. pneumoniae* strain Mu55. For all data, greyscale plot: no-antibiotic, paired control. Black contour: antibiotic-treated data.
Figures 8A, 8B, 8C, 8D, 8E, 8F:
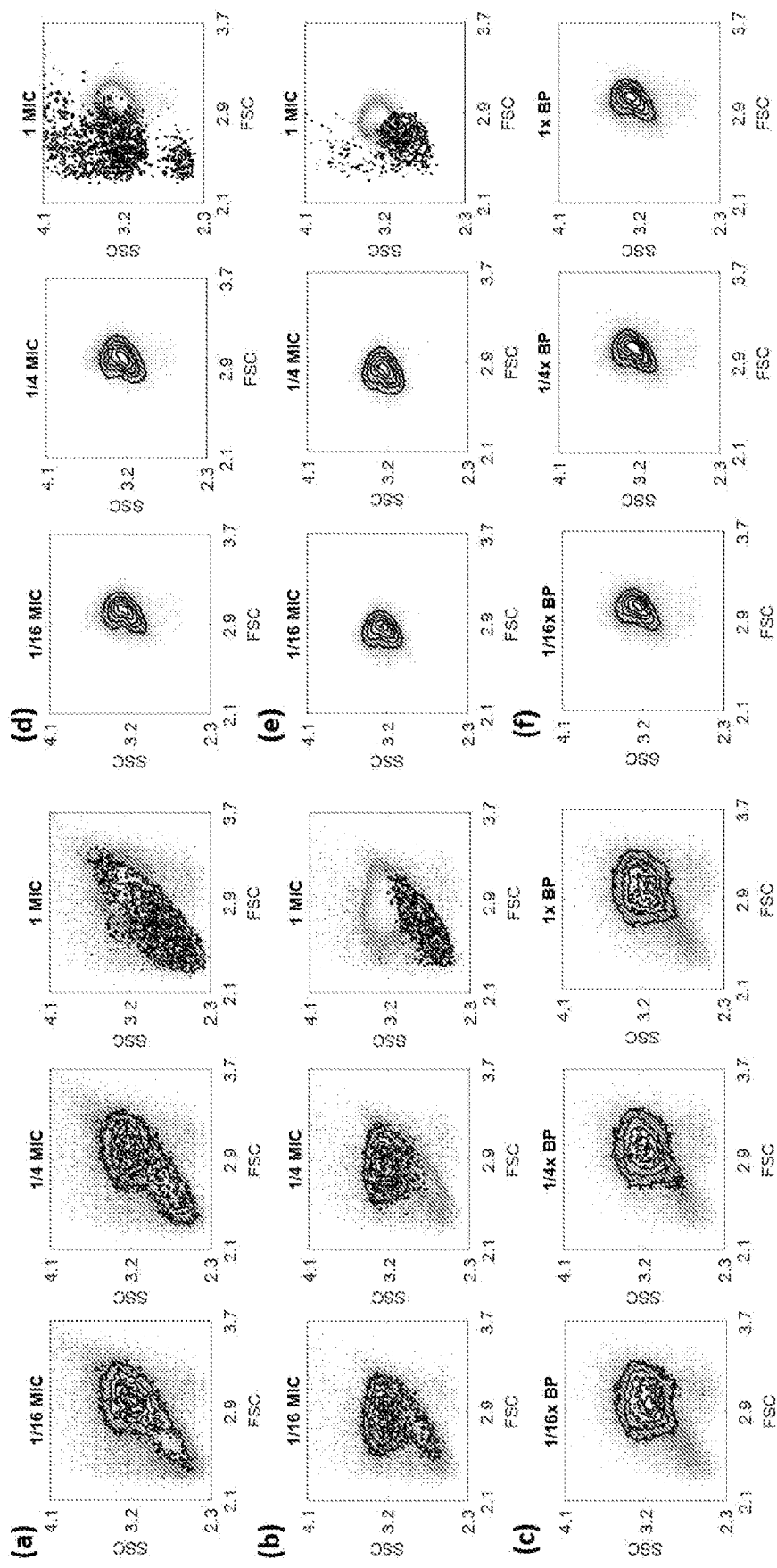
FIGS. 8A-8F. Bactericidal Antibiotic-induced scatter changes for *K. pneumoniae* strain Mu670. For all data, greyscale plot: no-antibiotic, paired control. Black contour: antibiotic-treated data.
Figures 9A, 9B, 9C, 9D, 9E, 9F:
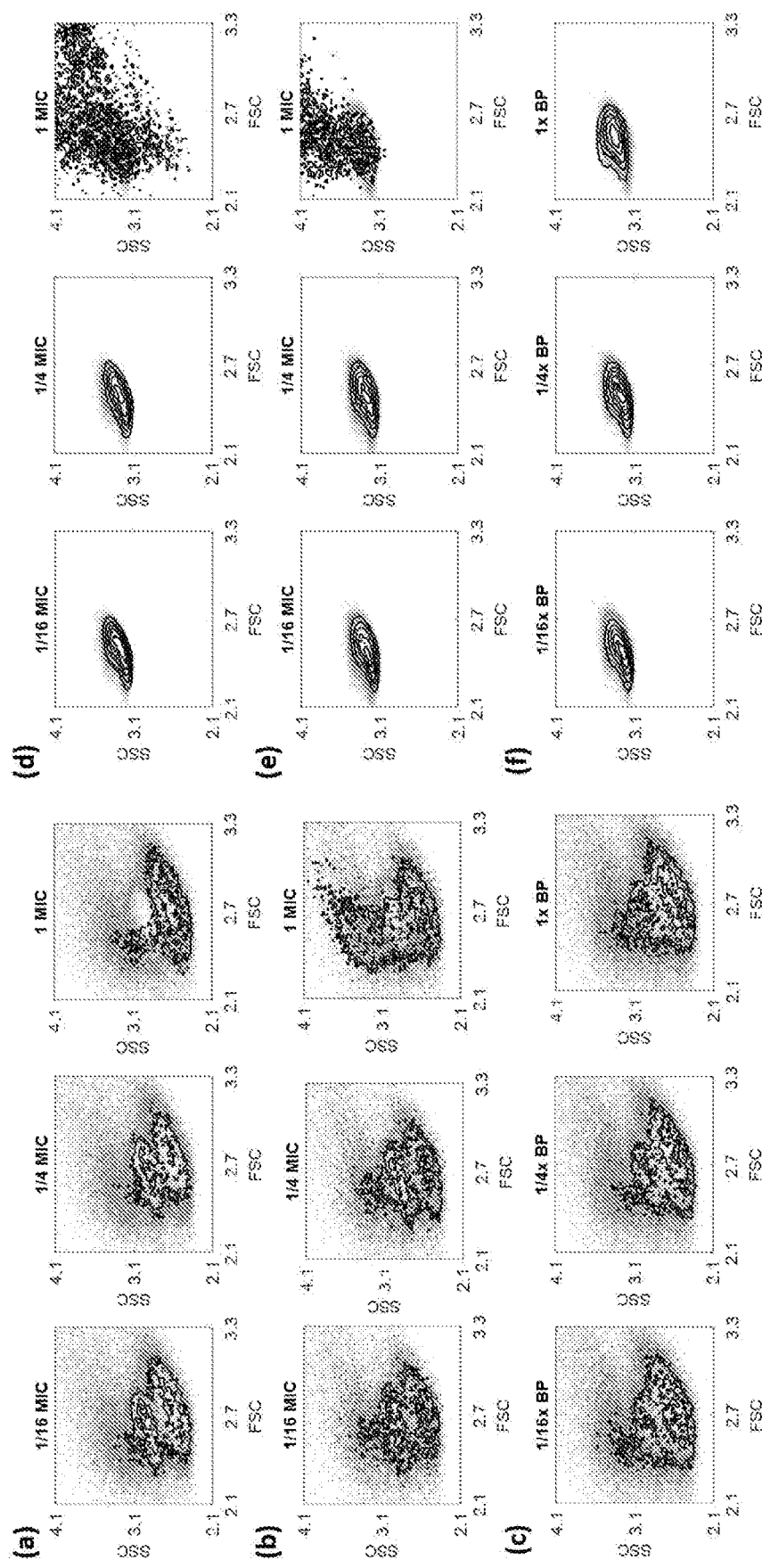
FIGS. 9A-9F. Bactericidal Antibiotic-induced scatter changes for *A. nosocomialis* strain M2. For all data, greyscale plot: no-antibiotic, paired control. Black contour: antibiotic-treated data.

Also matching its standard AST data, FAST shows that Mu14S is intermediate to gentamicin and when treated at the MIC, exhibits growth inhibition (FIG. 2B and FIGS. 5A-5F). When treated with tetracycline or ampicillin at each resistant breakpoint (16 µg/mL and 32 g/mL), however, Mu14S signals remained statistically unchanged. The PB-sQF fold distance average from triplicate data shows clear differences between the 1×MIC gentamicin data versus the paired-control (FIG. 2C). This confirms that the gentamicin sensitivity of Mu14S observed after blood culture[1] can also be observed on much shorter timescales with FAST. Overnight plating confirms that initial Mu14S counts were 3, 2, 5 and CFU/mL for tetracycline, gentamicin and ampicillin data after 10-fold dilution of the blood/bacteria mixture, corresponding to FAST being performed on whole blood samples containing ~30, ~20 and ~50 CFU/mL. Controls of identical treatment of 10% human blood samples without bacteria inoculation were also tested, yielding scattered light histograms that do not significantly change around the resistance breakpoints of Enterobacteriaceae under gentamicin, ampicillin, or tetracycline treatment (FIGS. 6A-6C). Thus, diluting bacterimic blood specimens 1:9 (v:v) directly into saponin-containing growth medium provides a path to ASTs within 8 hours from initial blood draw, with excellent results matching independent (36-44 hrs) MIC determinations from pure, overnight cultures (~$10^8$ CFU/mL) that could only be initiated after (~24 hr) positive blood culture.

Multidrug Resistant *K. pneumoniae* Isolates.

The same FAST procedure was applied to two multidrug-resistant *K. pneumoniae* clinical isolates, Mu55 and Mu670. Analogous to the *E. coli* data, *K. pneumoniae* growth inhibition is directly quantified with PB-sQF upon effective antibiotic treatment, and sensitivities are accurately determined. Importantly, when treated with antibiotics to which Mu55 or Mu670 were resistant, the scatter data (black contours) were not statistically different from each experiment's paired control (greyscale plots) as shown in FIGS. 7A-7F (Mu55), and FIGS. 8A-8F (Mu670). PB-sQF confirms that tetracycline is effective toward Mu670 and gentamicin is appropriate for both Mu55 and Mu670. The initial bacterial concentrations post 10-fold dilution were confirmed by plating to be ~8 CFU/mL for Mu55 and ~9 CFU/mL for Mu670, demonstrating that FASTs can be readily completed within 8 hours of initial blood draw on blood samples exhibiting <100 CFU/mL.

Multidrug Resistant *A. nosocomialis* Isolates.

Figure 3:
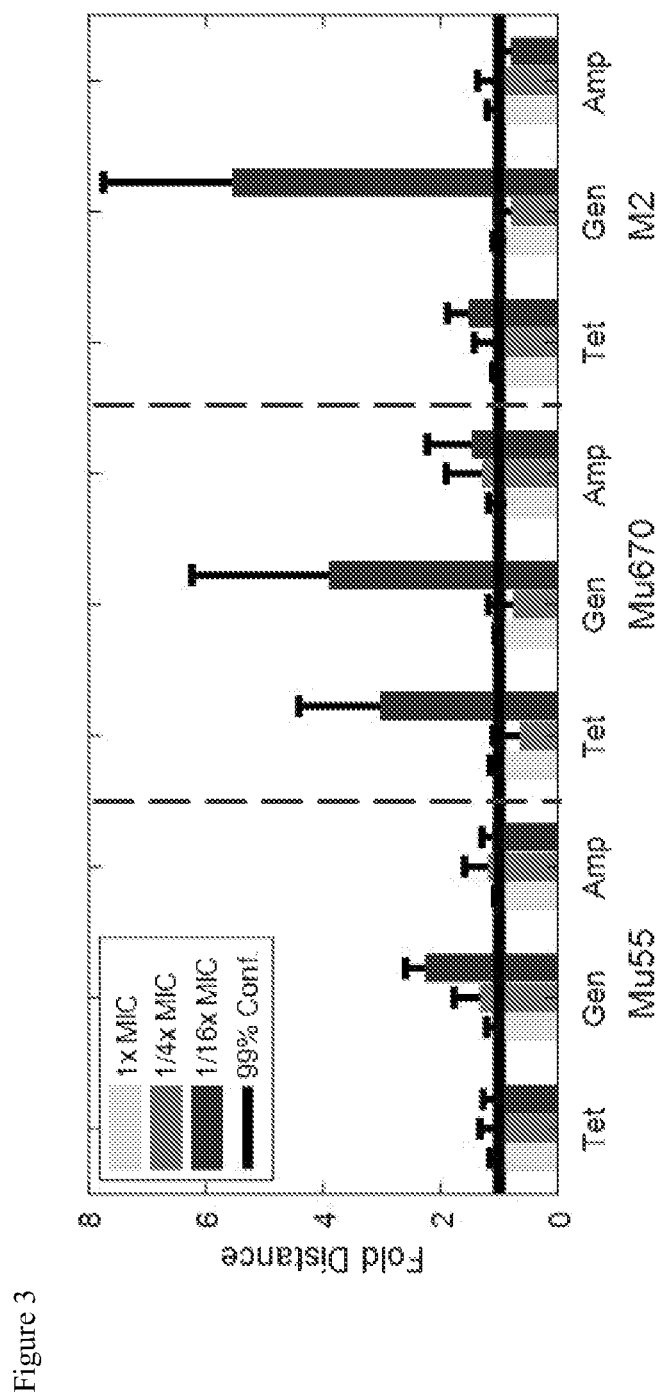
FIG. 3. FAST antibiotic-induced scatter signal changes for *K. pneumoniae* stain Mu55 and Mu670 and *A. nosocomialis* strain M2 reveal different susceptibilities. The PB-sQF result for each strain is shown in each segment. Mu55 (left) was treated with tetracycline at 16 µg/mL (resistance breakpoint) or gentamicin at 1 µg/mL (MIC) or ampicillin at 32 µg/mL (resistance breakpoint). Mu670 (middle) was treated with tetracycline at 2 µg/mL (MIC) or gentamicin at 4 µg/mL (MIC) or ampicillin at 32 µg/mL (resistance breakpoint). M2 (right) was treated with either tetracycline at 1 µg/mL (MIC), gentamicin at 2 µg/mL (MIC), or ampicillin at 128 µg/mL (resistance breakpoint for penicillin type antibiotic). As in FIG. 2C, the y-axis is the fold distance normalized by the 99% confidence level (thick black line equal to 1). The error bar is one standard deviation of each test result above and below the average.
Figures 4A, 4B, 4C, 4D, 4E, 4F:
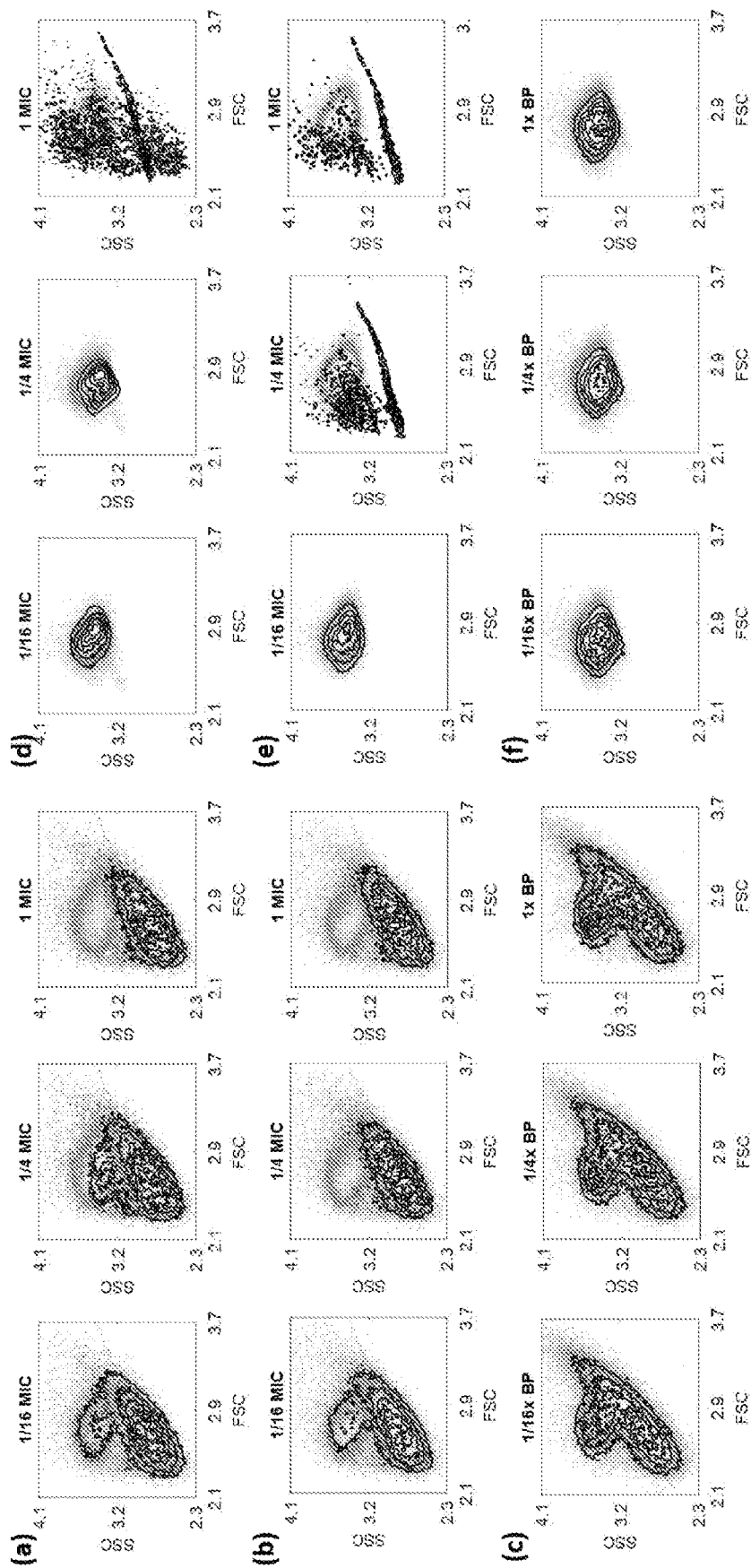
FIGS. 4A-4F. Bactericidal Antibiotic-induced scatter changes for *E. coli* strain Mu890. For all data, greyscale plot: no-antibiotic, paired control. Black contour: antibiotic-treated data.
Figures 5A, 5B, 5C, 5D, 5E, 5F:
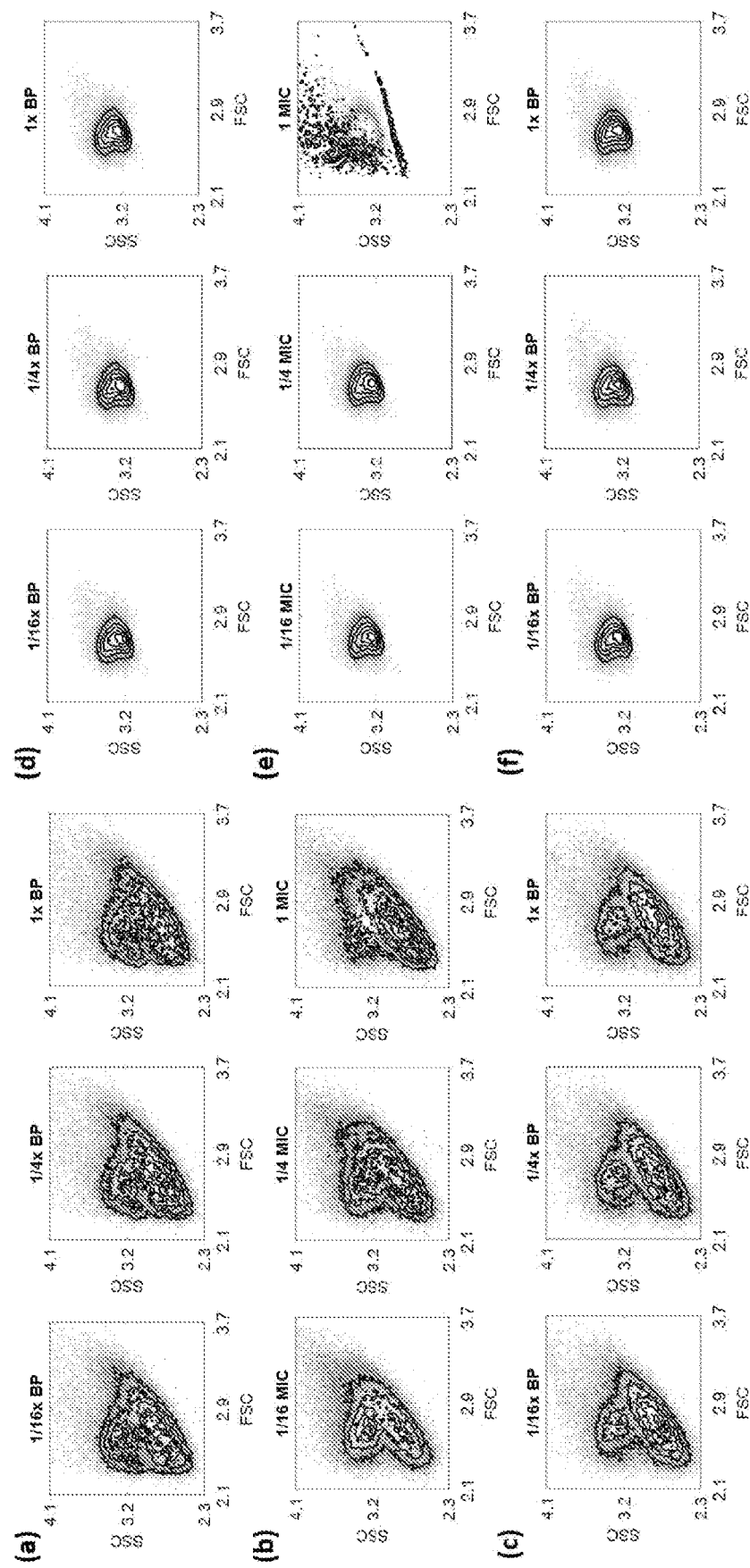
FIGS. 5A-5F. Bactericidal Antibiotic-induced scatter changes for *E. coli* strain Mu14S. For all data, greyscale plot: no-antibiotic, paired control. Black contour: antibiotic-treated data.

Obtainable in $<\frac{1}{8}$th the time of standard AST results, FAST on *A. nosocomialis* clinical isolate M2 spiked in 10% human blood (FIGS. 9A-9F) enabled its susceptibility profile to be similarly quickly determined. As with other species, PB-sQF reveals that M2 is resistant to ampicillin but susceptible to both tetracycline and gentamicin when assayed within 8 hrs of initial simulated blood draw (FIG. 3). Different from the ~$10^5$ CFU/mL *E. coli* and *K. pneumoniae* strains resulting from 2-hr preincubation, the final *A. nosocomialis* concentrations were ~$10^4$ CFU/mL, as confirmed by plating. Even with an order of magnitude fewer bacterial counts, the clear growth inhibition was readily quantified with the same procedure. As initial ~10 CFU/mL samples incubated for 5 hours are sufficient for analysis, ~10 doubling events are ideal to generate sufficient sample for FAST antibiotic panels to be performed on any bacteria. For the most common sepsis-inducing strains, including gram-negative *E. coli*, *P. aeruginosa*, and *Klebsiella* spp.,[45,46] 10 doubling events should be achieved within the total 2-hr pre-incubation and 3-hr incubation with antibiotics in 1:9 whole blood:standard bacterial media.

Discussion

Most cytometric-based bacterial viability tests utilize fluorescent dyes to assay live/dead populations after positive blood cultures, but have problems with many antibiotic/bacteria combinations. Here, it is shown that by using PB-sQF to characterize the differences between dataset, the changes in 2D scatter patterns are sufficient for a robust growth inhibition-based phenotypic AST directly from bacteria-containing blood. A scatter-only AST is more general to different bacterial strains since there is no staining problem as seen in the previous studies.[17,19] PB-sQF calculates the true linear distance between data sets so the data collect from different machines or different days can be directly compared. The data shown in FIGS. 2A-2C and FIG. 3 fluctuate from run to run due to the varying ratio between bacterial cells and blood debris resulting from sample processing. Also, when the blood debris counts are high, the signals can partially obscure the bacteria signal. Additionally, bacteria with different size and shape produce different scatter patterns that can increase overlap with the blood debris background. As a result, setting an artificial gate to discriminate bacteria counts is problematic when the bacterial identity is unknown. Without robust multidimensional statistics, unbiased by artificial gating, determining statistical distances between any two data sets that have different background signals is an outstanding challenge. PB-sQF calculates similar level of fold distances of the triplicate data from their own paired controls with different levels of background noise. With triplicate error bars included in the PB-sQF analysis, the 1×MIC data were statistically significantly different from the 99% confidence level.

To rapidly determine appropriate treatments for gram-negative bacteria, the inventors developed FAST to minimize time to result from initial blood draw. By selectively removing blood cells, FAST requires a total of only 8 hours to complete susceptibility testing. Using flow cytometry to acquire the entire distribution of bacterial responses to antibiotic exposure, PB-sQF statistical metrics directly quantify the differences between antibiotic-treated data and no-antibiotic paired controls. Consistent results are obtained even when data vary among different replicates, or if performed on different instruments. This procedure, without time-consuming overnight incubation and multiple serial subculturing, reduces the time to result from >60 hours to <8 hours total time from initial blood draw, with identical susceptibility determinations. Since rapid identification of the correct antibiotic treatment is crucial in treating suspected bacterial infections, FAST has the potential to greatly improve patient outcomes, while minimizing antibiotic resistance proliferation. While both bacterial identity and susceptibility profile are currently needed for appropriate treatment, CLSI breakpoints for the most common bacteremia-causing bacteria differ by <4-fold.[12] Thus, testing additional antibiotic concentrations to encompass the full susceptibility ranges of the most common bacteremia-causing pathogens could rapidly provide susceptibility information without waiting for much slower, post blood culture bacterial identity determinations. As the majority of blood stream infections are caused by gram-negative bacteria,[45,46] this approach offers a path to drastically improved patient outcomes, while still allowing for subsequent confirmation from standard post blood culture pathogen identification and ASTs.

Materials and Methods

Bacterial Strains and Antibiotics

All clinical isolates (*E. coli* strains Mu14S and Mu890, *K. pneumoniae* strains Mu670 and Mu55, *A. nosocomialis* strains M2) were obtained from the Georgia Emerging Infection Program (GEIP). The MIC of each isolate was determined by a clinical microbiology laboratory using post blood culture automated AST and confirmed using broth microdilution in our laboratory. The MICs of each strain were measured to be as follows. For *A. nosocomialis* strain M2, 1 µg/mL tetracycline, 2 µg/mL gentamicin, and >1024 µg/mL ampicillin. For *E. coli* strain Mu890, 1 µg/mL tetracycline, 8 µg/mL gentamicin, and >1024 µg/mL ampicillin. For *E. coli* strain Mu14S, >64 µg/mL tetracycline, 8 µg/mL gentamicin, and >1024 µg/mL ampicillin. For *K. pneumoniae* strain Mu55, >64 µg/mL tetracycline, 1 µg/mL gentamicin, and >1024 µg/mL ampicillin. For *K. pneumoniae* strain Mu670, 2 µg/mL tetracycline, 4 µg/mL gentamicin, and >1024 µg/mL ampicillin.

Fast

To simulate a blood specimen from a patient with bacteremia, the isolates were grown, diluted to the desired CFU/mL in blood (ZenBio, Research Triangle Park, NC) and saponin was added to achieve the final diluted sample. Initial bacterial cultures were prepared using Luria-Bertani (LB) broth for (*E. coli*) or cation-adjusted Mueller-Hinton broth (CAMHB). The fresh bacterial cultures started from ~0.05 optical density (OD) by inoculating a 6-mL fresh growth medium with overnight culture were grown in an incubator shaker (MaxQ 4000, Thermal Fisher Scientific, Waltham, MA) at 37° C. and 225 rpm. After the culture reached mid-log phase, bacteria were collected and diluted into ~10 CFU/mL through serial 10-fold dilutions. Bacterial densities were determined by plating onto LB plates. The final 10-fold dilution was performed by adding 500 µL of 100 CFU/mL into 4500 µL of 10% human blood in medium.

A 2.5% (w/v) of saponin solution was prepared, sonicated (Branson 2510, Emerson, St. Louis, MO) for 20 minutes and spun down with a clinical centrifuge (Centrific Model 228, Fisher Scientific, Waltham, MA) for 4 minutes. The supernatant cleared of particulates was collected. 500 µL of 2.5% saponin was then added to the 5 mL of 10% human blood sample with ~10 CFU/mL, described above and the mixtures were shaken at 300 rpm for 15 minutes at 37° C. After the saponin treatment, the bacteria were pelleted and washed with 2 mL of phosphate buffered saline (PBS) (Life Technologies, Carlsbad, CA) using a clinical centrifuge for 2 minutes. Bacterial growth medium (2.5 mL) was then added to the tube and incubated for 2 hours at 37° C. and 225 rpm.

After the 2-hour incubation, 500-µL aliquots of the suspension were added to each of 4 wells in a 12-well microtiter plate that contained 500 µL of growth medium with or without antibiotic at 2-fold of specified concentrations. The plate was then incubated at 37° C. for 3 hours. Bacteria were collected by centrifugation (Centrifuge 5417R, Eppendorf) and resuspended in 200 µL of PBS for flow cytometry detection. To ensure each clinical isolate was tested at its MIC values of the tested antibiotics, the initial bacterial cultures at the 1000 CFU/mL dilution were also tested for each experiment (FIGS. 4A-4F, 5A-5F, 7A-7F, 8A-8F, and 9A-9F), confirming that the antibiotic concentrations indeed inhibited bacterial growth.

Flow Cytometry

Cytometric data were collected by BD LSRFortessa flow cytometer (Becton Dickinson, Franklin Lake, NY) equipped with a 100 mW, 488 nm laser for the scatter signal. Thresholds were set on both forward and side scatter to exclude noise observed when running a phosphate buffered saline blank solution. Data were recorded with FACSDiVa provided by BD. For FAST data, either 100,000 events were collected or collection was stopped when the sample volume was nearly depleted. Flow cytometry data were exported into .fcs files for further analysis and display in MATLAB 2016a (MathWorks, Natick, MA).

PB-sQF Test Statistics

The statistical tests were performed in MATLAB 2016a on an Intel® Core™ i7-4790 CPU (3.60 GHz) machine, equipped with 12.0 GB RAM running MS Windows 10. The PB-sQF procedure was as described in our previous publication.[1] For each data set, thresholds were applied to both dimensions to include data points lie within the range from 5 to $10^5$ to exclude outliers. PB-sQF starts with the probability binning approach developed by Roederer et al.,[37,38] but uses a different and linear statistical distance metric. The probability binning approach treats the original data as the initial bin. The variances of all dimensions (here, forward scatter and side scatter) were calculated and the initial bin was divided into 2 daughter bins at the median of the highest variance dimension. Data points on the median were randomly assigned to the 2 daughter bins. The same procedure was recursively applied to split each daughter bin into its daughter bins, until the designated number of bins were generated. All data were analyzed with 128 bins. Probability binning generates irregularly shaped bins containing similar numbers of counts. The binning patterns are adaptive and represent the data with more (and smaller) bins in regions where the data is most highly concentrated. The same adaptive binning procedure is applied to both no-antibiotic controls and the antibiotic-treated samples. Going beyond probability binning, the centroids of the data within each bin and weights (normalized numbers of counts in each bin, relative to the total counts) were then calculated and stored for calculation. These are the "signatures" of the data, and are unique to the described PB-sQF approach. In this manner, data with ~100,000 bacterial counts in any number of dimensions is reduced to 128 adaptive bins (and corresponding centroids)/data set for fast distance calculations among data.

Bins are numbered for control (c) and sample (s) centroids in the order that the bins are created in the probability binning process, with N total bins. The weight for each bin is the number of counts per bin divided by the total number of counts. As with non-adaptively binned quadratic form statistics, the weight vector is the collection of the weights from the control and sample data:

$$\text{Weight} = (w_c^1, w_c^2, \ldots, w_c^N, -w_s^1, -w_s^2, \ldots, -w_s^N)$$

The negative sign for the sample weights ensures that the difference between the control and sample is calculated in the following matrix multiplication.

The centroid is the multidimensional median of the data in each bin and the calculation is described below in the "Geometric quantile" section. The centroid matrix is written as:

$$\text{Cent} = (C_c^1, C_c^2, \ldots, C_c^N, C_s^1, C_s^2, \ldots, C_s^N)$$

The notation is the same as in the weight vector. "Cent" is a matrix listing all the centroids from control and sample, with each column representing a centroid and each row representing one dimension.

The centroids and weights were then used to calculate the test statistics as described in sQF[39,40]. First, a similarity matrix is constructed. The matrix elements at $i^{th}$ row and $j^{th}$ column, $A_{ij}$, in the similarity matrix, A, is defined as:

$$A_{ij} = 1 - \frac{L[Cent(i), Cent(j)]}{\sqrt{\#\text{dimension} \cdot L_{max}}}$$

The first term is a 2N×2N matrix of 1's and the second term is the dissimilarity matrix. The numerator, L[Cent(i), Cent(j)], calculates all pairwise Euclidean distances between multidimensional centroids i and j, for both the control and the sample. The denominator is the maximum distance to normalize the calculated distance. $L_{max}$, is the maximum distance in one dimension. Since we have the same maximum range for each dimension, the maximum distance for n dimensions is $\sqrt{n} \cdot L_{max}$. When the two centroids are identical, the numerator goes to 0 and thus no dissimilarity exists. Conversely, when the maximum difference occurs, the $2^{nd}$ term goes to 1 due to normalization. The similarity matrix, A, is the logical opposite of the dissimilarity matrix so the dissimilarity matrix is subtracted from the 2N×2N matrix of 1's. Note that the diagonal elements, the similarity of centroid i and i, is always one. Each test statistic (statistical distance, D) were then calculated in quadratic form:

$$D = \sqrt{\text{Weight} \cdot A \cdot \text{Weight}^T}$$

$\text{Weight}^T$ is the transpose of the Weight vector.

Confidence Level Estimation and Fold Distance

The bootstrap method was used to estimate the 99% confidence level of the no-antibiotic control and the $\frac{1}{16} \times$ MIC data. By calculating the 99% confidence levels from small sample size sub-distributions, bootstrapping can estimate the confidence level at the data sample size accurately. 70 sub-distributions with the sample size ranging from 4*(number of bins) to ($\frac{1}{10}$ of sample size) with 20 steps, were randomly sampled from the $\frac{1}{16} \times$MIC data and the paired no-antibiotic control. The lower bound, 4*(number of bins), was chosen to prevent zero counts per bin. The upper bound, ($\frac{1}{10}$ of sample size), was set to ensure the sampling process was random. All 140 sub-distributions were binned and the centroids and weights were calculated as described in "PB-sQF test statistics". Test statistics were calculated between all 70 sub-distributions from the $\frac{1}{16} \times$MIC data and the 70 paired controls. Since all the sub-distributions were sampled randomly thus were different from each other, the test statistics yield a distribution (biological variability) and the 99% confidence level for each sample size was determined. The confidence levels decreased as a function of sub-sample size since all the sub-distributions come from the same mother distribution and the larger the sample size, the better the estimation of the mother distribution. The distribution of the 99% confidence level should approximate a Gaussian distribution at large sample size according central limit theory, thus the uncertainty in estimating the confidence level can be described with an equation used to estimates the standard error of the sample mean:

$$\frac{a1}{\sqrt{n}},$$

here n is the sample size and a1 is the standard deviation of the population. The 99% confidence level at sample size n, Conf(n), can then be described by the following equation:

$$Conf(n) = a0 + \frac{a1}{\sqrt{n}}$$

where a0 is the confidence level of the population. The confidence level at sample size n converges to the population's confidence level as the uncertainty decreases. From the fitting, we can get the confidence level of the mother distribution with sample size n. For our pure culture control, n=100,000 counts. While in FAST, n varies. The test statistic of each antibiotic-treated sample was then normalized with the calculated confidence level and turned into fold distance relative to its paired control for direct comparison among different samples and replicates.

Error Bar Determination

Two different uncertainties contribute to the error bars. The first is biological variability and was determined by the standard deviation of the triplicate data. The second is the uncertainty in centroid position associated with the dispersion of data points in each bin. This uncertainty is determined by the median absolute deviation (MAD) of data within each bin. MAD was chosen over the standard deviation of each bin because MAD is more robust toward outliers. The MAD is calculated as follows:

$$\text{MAD} = \text{median}[\text{abs}[X_i - \text{centroid}]]$$

The median of the absolute distance between each data point, $X_i$, and the centroid of each bin.[41,42] The standard deviation can be estimated from MAD by:

$$\sigma_{perbin}^{MAD} = \frac{MAD}{\varphi^{-1}\left(\frac{3}{4}\right)}$$

where $\varphi^{-1}$ is the inverse of the cumulative distribution function or the quantile function.[42] Thus, the standard deviation (without the influence of outliers) can be calculated by dividing the MAD with the 75% quantile (See section "Geometric quantile", below). The final binning uncertainty for each replicate i, $\sigma_i^{binning}$, was estimated by propagating the uncertainty from each bin, $\sigma_{perbin}^{MAD}$.

Since all triplicate data were sub-samples from the same unknown population, the uncertainty from each replica was further pooled together to estimate the uncertainty of binning for the population as follows:

$$\sigma_{binning}^2 = \frac{\sum_{i=1}^{k}(n_i-1)(\sigma_i^{binning})^2}{\sum_{i=1}^{k}(n_i-1)}$$

in which k=3 for triplicate data. $n_i$ is the sample size of each replicate.

The biological variation uncertainties from triplicate data and binning errors were propagated together to get the final uncertainty.

$$\sigma^2 = \sigma_{Tri}^2 + \sigma_{binning}^2$$

The error bars in the bar charts are one standard deviation above and below the test statistic value.

Geometric Quantiles

Geometric quantiles were used for calculating the multi-dimensional medium of each bin as the centroid and for estimating the standard deviation from MAD. The geometric quantile, Q, is defined as the data point that minimizes the following target function as described by Chaudhuri[43]:

$$f(\vec{Q}^{(m)}) = \sum_{i=1}^{n}\left\{\left|\vec{X_i} - \vec{Q}^{(m)}\right| + \vec{u}\cdot\left(\vec{X_i} - \vec{Q}^{(m)}\right)\right\}$$

in which n is the number of data points in each bin; $\vec{X_i}$ is the data point, and $\vec{Q}^{(m)}$ is the quantile of the $m^{th}$ iteration; $u=2\alpha-1$, where $\alpha$ is fractional quantile. For example, $\alpha=0.5$ for media (50% quantile) and the target function reduces to $$f(\vec{Q}^{(m)}) = \sum_{i=1}^{n}\left\{\left|\vec{X_i} - \vec{Q}^{(m)}\right|\right\}.$$

The 50% quantile is the Q that minimizes the sum of distances between each data point to Q. For other quantiles, the second term in the target function is not zero and takes the deviation from the median into account. To minimize the target function, the quasi-Newton method was used to solve the unconstrained minimization problem.

Our initial guess, $\vec{Q}^{(0)}$, is the 1-D quantile in each dimension. $\vec{Q}^{(1)}$ is estimated using the following equations:

$$\vec{Q}^{(m+1)} = \vec{Q}^{(m)} + \vec{s}^{(m)}$$

$$\vec{s}^{(m)} = -\frac{\nabla f(\vec{Q}^{(m)})}{\nabla^2 f(\vec{Q}^{(m)})}$$

in which $\vec{s}^{(m)}$ is the increment determined by the first- and second-order derivative of the target function at the current iteration. For each step, $f(\vec{Q}^{(m+1)}) < f(\vec{Q}^{(m)})$ must be satisfied. If not, a better $\vec{Q}^{(m+1)}$ is needed.[44]

The iteration stops when either (1) the iteration has been carried out 50 times or (2) the relative gradient in Q is smaller than the stopping criteria we set. The relative gradient is:

$$relgrad(Q) = \frac{\frac{f(\vec{Q}^{(m)} + \delta) - f(\vec{Q}^{(m)})}{f(\vec{Q}^{(m)})}}{\frac{\delta}{\vec{Q}^{(m)}}}$$

In this work, the iteration was stopped when relgrad(Q) is smaller than $10^{-4}$.

Example 2—Development of Saponin Lysis Step

Pre-Blood Culture AST Condition Search

To find the experimental conditions to remove blood cells, the detection limit of the flow cytometer was tested. Then, various conditions to separate the bacteria from blood samples, including serum separator tubes (SST) and saponin, were examined.

Varied Incubation Time with *E. coli* Only Samples

When taking flow cytometry data, background signals that come either from electronic noises or small particles in the solution always compete with signals of interest. Background noise obscures the events of interest when the signal is weak, as in the case of patients with sepsis. Since blood cells add more noise to the system, it is important to understand the detection limit of flow cytometric bacteria signals even before blood cells are added.

Blood Cells Removal with Serum Separation Tube

Serum separator tubes (SST) are routinely used in the clinical lab to separate blood cells from serum for medical tests. When spinning down the blood sample in the SST, the blood cells penetrate into the gel layer at the bottom of the tube while the serum stays at the top. When the blood sample contains bacteria, it has been reported that the bacteria cells would be spun down on top of the gel layer thus separating from the blood cells.

To examine whether SST can successfully separate bacteria from blood cells, three samples were tested including: (1) 10% human blood only, no *E. coli* control, (2) 10% blood spiked with $10^6$ CFU/mL of *E. coli* (ATCC 33456) and (3) 10% blood sample spiked with $10^7$ CFU/mL of *E. coli*. All three samples were loaded to the SSTs, inverted five times, waited for 30 minutes and spun down with a clinical centrifuge for ten minutes as the manufacturer (Becton Dickinson, Franklin Lake, NY) suggested. The supernatant (serum) was discarded, and 980 µL of LB broth was added to resuspend the bacteria. The solution was transferred to a 12-well plate that was loaded with 20 µL of MH-IR786 (fluorescence dye, final MH-IR786 concentration 900 nM) and incubated for 4.5 hours. Even though it has been shown that the fluorescent signals from MH-IR786 fluctuated from data to data, MH-IR786 was used here since it has been shown that it can only be taken up by bacteria cells. As a result, MH-IR786 should help distinguish the bacteria cells from blood cells. After the incubation, samples were collected and analyzed by flow cytometry.

Figures 10A, 10B, 10C, 10D:
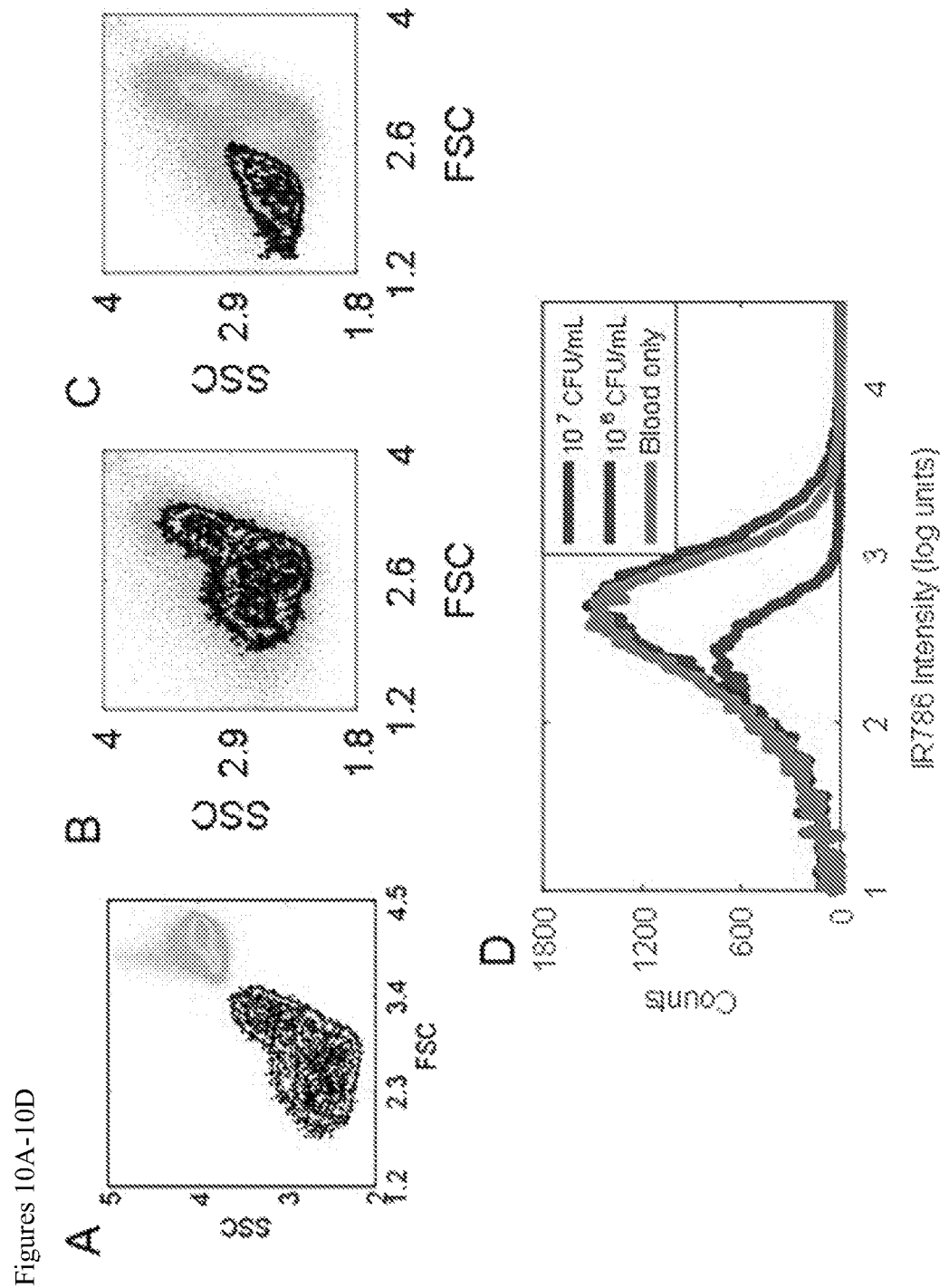
FIGS. 10A-10D. Failed attempts of *E. coli* separation using SST.

As shown in FIG. 10A, the gel layer from the SST generated high cytometric background. As a result, even the blood-only data is dominated by the signal from the SST generated background. This high noise also obscured the bacteria signals. The 10% blood only scatter data looks very similar to the *E. coli* spiked, 10% human blood data even when the inoculation concentration was as high as $10^6$ CFU/mL and had been incubated for 4.5 hours (FIG. 10B). A discernible scatter difference only appeared when the initial inoculated concentration was $10^7$ CFU/mL (FIG. 10C). The 1D fluorescence signal also only shows differences with the $10^7$ CFU/mL spiked blood sample. The fluorescence signals of the $10^7$ CFU/mL sample, however, was lower than the blood only sample (FIG. 10D), which contradicts the previous observation that mammalian cells do not uptake MH-IR786, or MH-IR786 is retained by the gel layer from the SST. With the high scatter backgrounds introduced by the gel layer of a SST, it would be difficult to detect any bacterial signal even after amplification.

As a result, SST was excluded from further study.

Blood Cell Removal with Saponin

Although the blood cells were successfully removed by SST, the high background from the gel layers made it difficult to detect bacterial signal. Saponin, on the other hand, does not generate much background signal itself. Instead of removing the blood cells, it lyses them without affecting bacterial growth. The inventors then studied the hemolysis effect of saponin was characterized, the MH-IR786's ability to distinguish blood cells from bacteria was investigated and a pre-blood culture AST with sheep blood was demonstrated.

Effect of Saponin and MH-IR786 Staining

Figures 11A, 11B, 11C:
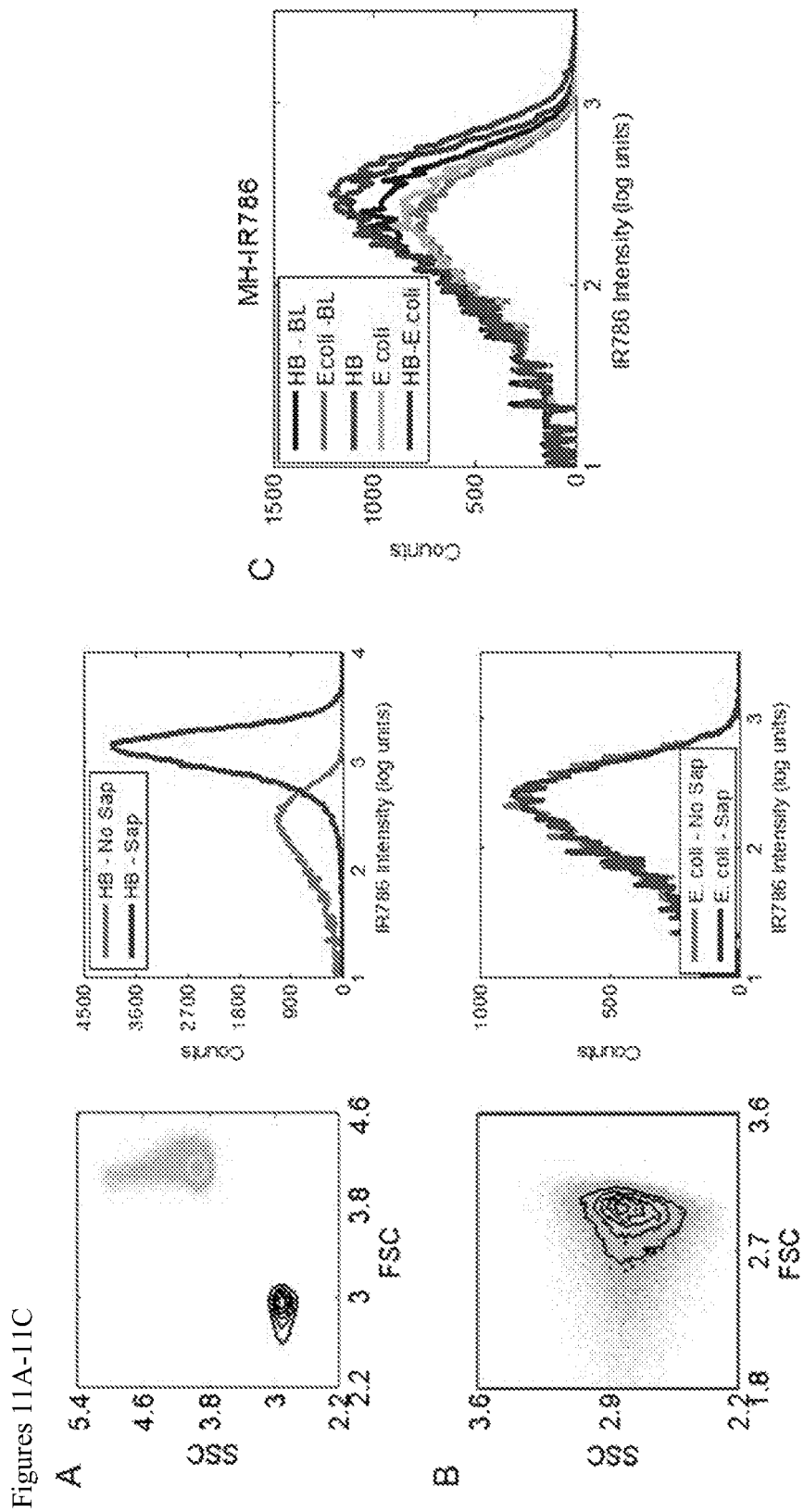
FIGS. 11A-11C. Saponin-treated human blood and *E. coli*. Flow cytometry data for (FIG. 11A) 10% human blood.

To test saponin's lysis ability, 100 μL of 1% saponin was added to 100 μL of human blood with 800 μL of LB and incubated at 37° C. for 10 minutes. The lysed 10% blood solution was then spun down, and washed with PBS. The pellet was then resuspended in 980 μL of LB, loaded to a 12-well plate with 20 μL of 45 μL of MH-IR786 and incubated for an hour. With the saponin treatment, the scattered-light signal clearly shifted to the lower left corner with smaller side and forward scatter signal (FIG. 11A). Since saponin lyses the blood cells, the smaller scattered-light signals showed that the cells were indeed damaged and broken into debris. The fluorescence signal, probably because of increased accessibility of MH-IR786 into damaged cells, was higher when the blood cells were lysed (FIG. 11A). As for *E. coli*, neither the scatter data nor the fluorescence signal changed with or without saponin treatment (FIG. 11B) which is inconsistent with the previous studies showing that *E. coli* is not effected by saponin. When comparing the fluorescence intensities between MH-IR786 stained human blood cells and *E. coli*, the fluorescence intensity was not higher in the *E. coli* only data. Combining with the fact that the blood cells debris generated higher fluorescence intensity than did the no saponin sample, MH-IR786 is most likely not actively taken up by the healthy bacteria.

Pre-Blood Culture AST with Sheep Blood

To search for the condition to separate bacteria from the blood cells, sheep blood was used as a substitute for human blood. In order to remove the blood cells that have a concentration that is $10^6$ to $10^7$ times higher than the bacteria, 100 μL of 10% (w/v) saponin was added to 1 mL of sheep blood that was spiked with either 100 μL of LB or $10^4$ CFU/mL *E. coli* strain ATCC 33456 (final concentration ~$10^3$ CFU/mL) and incubated for 15 minutes at room temperature to lyse the blood cells. The same procedure was applied to 12 samples loaded in eppendorf tubes. These samples were then washed with PBS and resuspended in 500 μL L B broth. All 12 samples were added to the 12-well plate loaded with 480 μL of LB broth and/or penicillin g with 2× higher desired concentrations and 20 μL, 45 μM of MH-IR786. The plate was incubated for 5 hours. Each sample was then collected and analyzed by flow cytometry.

Figures 12A, 12B, 12C:
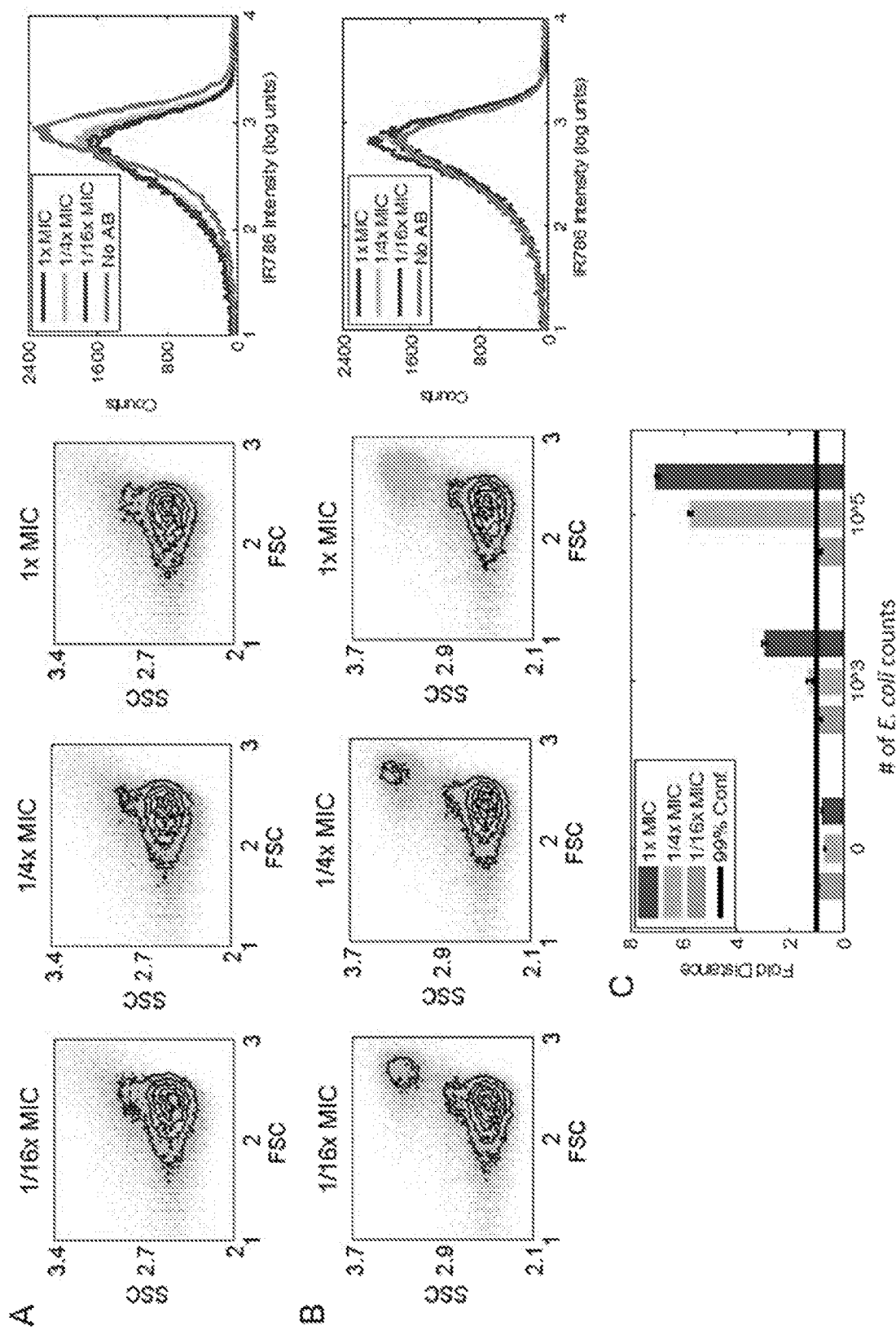
FIGS. 12A-12C. Pre-blood culture AST with sheep blood. Flow cytometry data for (FIG. 12A) 100% sheep blood only.

The cytometric data for blood-only samples (100% blood) remained very similar to each other from no-antibiotic to 1×MIC of penicillin g (FIG. 12A) while clear growth inhibition can be observed at 1×MIC in the 1000 CFU/mL of *E. coli* spiked sample (FIG. 12B). The differences in the 3D cytometric data are seen in PB-sQF results with the blood only data showing no statistically significant difference between each other while both 1000 CFU/mL and $10^5$ CFU/mL show clear increment of distance increases from $\frac{1}{16}$×MIC to 1×MIC (FIG. 12C).

Characterize the Killing Efficiency of Blood Cells over Bacteria

The same blood cell lysis condition that was found for the sheep blood was applied to the human blood sample. The lab-strain *E. coli*, however, were not recoverable from the human blood sample as they were in the sheep blood, but were killed by the human blood instead.

Figures 13A, 13B:
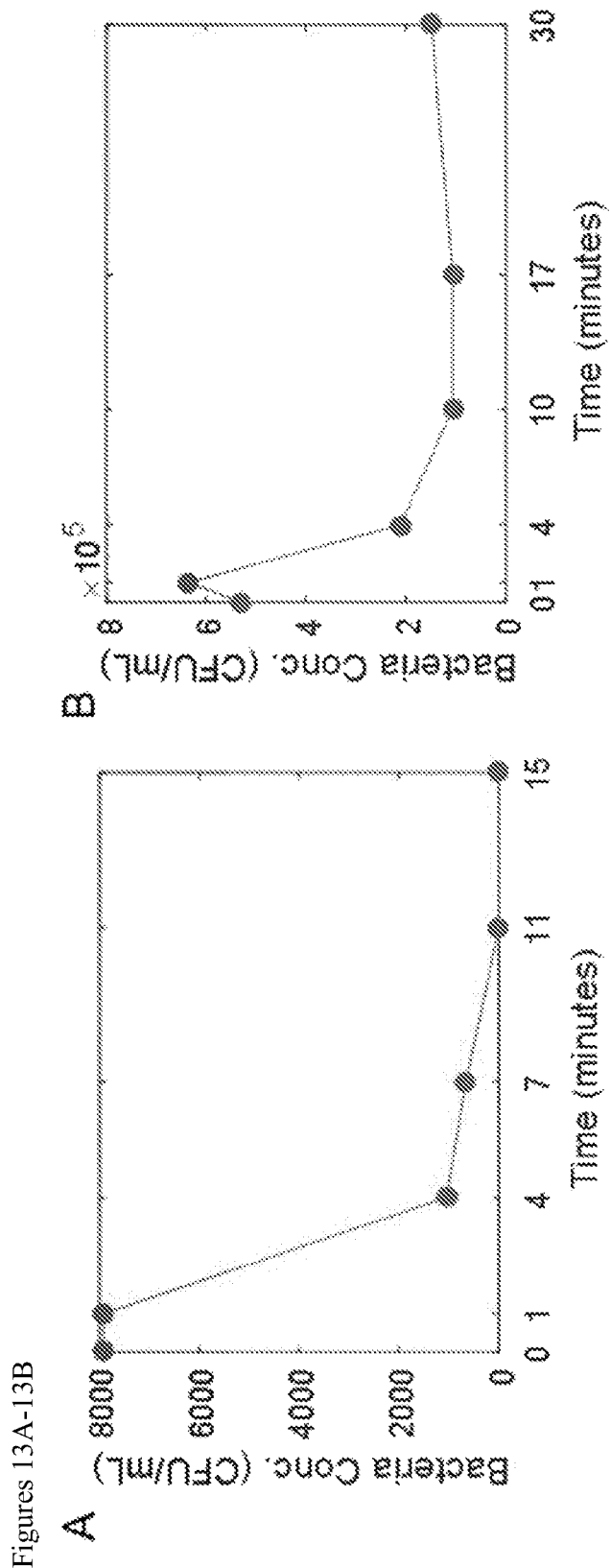
FIGS. 13A-13B. Human blood cells kill non-blood stable *E. coli*.

To demonstrate this, 800 μL of $10^5$ CFU/mL lab strain *E. coli* were incubated with 7200 μL of 10% human blood, and 800 μL of 1% saponin for 15 minutes. 1 mL of sample was taken out for overnight plating at 0, 1, 4, 7, 11 and 15 minutes of the incubation time. These 1 mL samples were diluted and plated overnight for colony counting. As shown in FIG. 13A, the colony counts kept decreasing from 1 minute of incubation time to 11 minutes when all of the *E. coli* were killed (no colonies detected). This shows that even with the present of saponin, $10^4$ CFU/mL of the lab strain *E. coli* was readily killed by 10% human blood in 11 minutes. As a result, the same procedure, recovering 1000 CFU/mL of the lab strain *E. coli* from 100% of sheep blood, did not work in human blood.

Since bacteria isolated from blood should have a higher resistance to blood cells, the multidrug-resistant *E. coli* clinical isolate Mu14S was tested. Different from the lab strain *E. coli*, $10^5$ CFU/mL of Mu14S were incubated with 10% human blood without saponin for 30 minutes. 1 mL of sample was taken out for overnight plating at 0, 1, 4, 10, 17, and 30 minutes. The colony counts dropped for the first 10 minutes but remained stable and probably actively growing from 10 to 30 minutes. This shows that the clinical isolates indeed survived in human blood as the case in sepsis patients. Saponin was therefore selected for use in lysing blood cells preferentially over bacteria. Since the bacteria count in a blood sample from a sepsis patient is lower than 100 CFU/mL and 10% blood was used in the FAST procedure (10 bacterial counts in each sample), the saponin incubation time was determined to be 15 minutes to prevent all the bacteria from being lysed due to longer incubation time. This was a consequence of spiking bacteria into blood. In infected blood from actual patients, typical bacterial loads of the blood-stable pathogens in bacteremic adults are <100 CFU/mL blood. Spiking even blood-stable isolates into blood kills some of the bacteria, with a subpopulation surviving. Consequently, to determine actual CFUs, spiked blood was plated at each step. Saponin enables recovery of even these low CFUs from blood background.

Example 3—FAST with Low Bacterial Counts

Active blood infections often present with ~100 CFU/mL blood for adults and ~1000 CFU/mL blood in pediatric patients. Because of these low CFU numbers, speed in ASTs from blood must effectively deal with low bacterial counts while rejecting often overwhelming blood background signals. The inventors developed a combined saponin-based approach to selectively lyse blood cells while retaining viable bacteria and allowing bacterial scatter signals to be visualized for effective ASTs. Changes in morphology can be used when high numbers of bacteria are measured through flow cytometry, but fast ASTs require many fewer bacteria to be analyzed, reducing statistical significance. This challenge was addressed by 1) replacing morphological changes with growth inhibition at various antibiotic concentrations and 2) being able to assess biovariability-based error through up-sampling and bootstrapping for even just a single replicate.

While both morphology and growth inhibition occur upon exposure to antibiotics near the minimum inhibitory concentration, standard ASTs are based on growth inhibition alone. The presence of bacteria is clearly indicated by the presence of a particular scattering peak in the multidimensional histogram. This is much more sensitive and less affected by background than is shifts in a peak resulting from morphological changes upon antibiotic exposure. Consequently, after saponin-based blood removal, growth inhibition-based ASTs in the flow cytometer are much more effective at low bacterial counts. For even a few hundred counts, the presence of a bacterial population can be readily assessed with flow cytometry, but error bars and statistical distances must be properly determined relative to no-antibiotic controls. When too few counts for triplicate runs exist, control and each antibiotic exposure histograms are treated as probability distributions that are representative of the true mother distribution for each condition. Each histogram is binned (either adaptively with probability binning or using regular bins) and the distribution of data within each bin is determined. Upsampled distributions within each bin are then proportionally generated to scale from the few hundred counts to 100,000 counts. These upsampled distributions are then used to bootstrap the control-antibiotic concentration distance to each original sample count size (few hundred counts) for accurate confidence limit determination. In the event of high background, the low count distributions can be adversely impacted by outliers that arise from non-bacterial signals. These can be first removed by calculating the outliers and using support vector machines to classify individual cytometric events as being part of or apart from the true distribution. This provides a statistically robust framework to reject the few data points that may otherwise skew the upsampled distribution from the low count data. With this procedure, accurate confidence levels can be obtained for very low count data, resulting in much more robust and faster antibiotic susceptibility testing at very low bacterial counts, even on single replicates.

Figure 14:
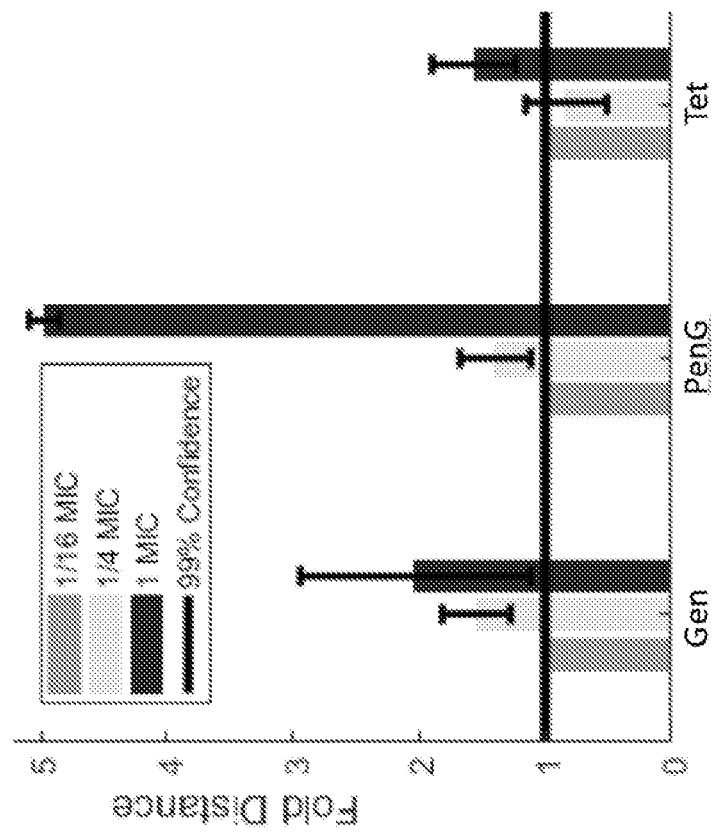
FIG. 14. Bactericidal Antibiotic-induced changes for low counts of *E. coli*. Lab-strain *E. coli* (ATCC) ASTs performed with 500 counts by flow cytometry with gentamicin (Gen), penicillin G (PenG), and tetracycline (Tet) each at MIC, ¼ MIC and ¹⁄₁₆ MIC. This strain is seen to be sensitive to all three antibiotics, as the bars extend beyond the 99% confidence line.

Bacteria recovery from blood has been demonstrated with our preliminary results at relevant BSI bacterial loads, enabling histograms from as few as 300 CFU to be used for each sample. The inventors have demonstrated excellent AST results with 500 CFU/sample (FIG. 14), with bootstrapping yielding quantitative confidence bounds with biovariability. With purification and appropriate bootstrapping for confidence level determination, additional incubation steps for increasing bacterial CFUs can be minimized to increase AST speed. Results should be applicable to both gram negative and gram positive pathogens.

While several possible embodiments are disclosed above, embodiments of the present disclosure are not so limited. These exemplary embodiments are not intended to be exhaustive or to unnecessarily limit the scope of the disclosure, but instead were chosen and described in order to explain the principles of the present disclosure so that others skilled in the art may practice the disclosure. Indeed, various modifications of the disclosure in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

REFERENCES

1. Huang T-H, Ning X, Wang X, Murthy N, Tzeng Y-L, Dickson R M. Rapid Cytometric Antibiotic Susceptibility Testing Utilizing Adaptive Multidimensional Statistical Metrics. Analytical Chemistry 2015; 87:1941-1949.
2. Kreger B E, Craven D E, McCabe W R. Gram-negative bacteremia. IV. Re-evaluation of clinical features and treatment in 612 patients. Am J Med 1980; 68:344-55.
3. Kollef M H. Broad-Spectrum Antimicrobials and the Treatment of Serious Bacterial Infections: Getting It Right Up Front. Clinical Infectious Diseases 2008; 47:S3-S 13.
4. Fraser A, Paul M, Almanasreh N, Tacconelli E, Frank U, Cauda R, Borok S, Cohen M, Andreassen S, Nielsen A D and others. Benefit of appropriate empirical antibiotic treatment: thirty-day mortality and duration of hospital stay. Am J Med 2006; 119:970-6.
5. Ibrahim E H, Sherman G, Ward S, Fraser V J, Kollef M H. The Influence of Inadequate Antimicrobial Treatment of Bloodstream Infections on Patient Outcomes in the ICU Setting*.
Chest 2000; 118:146-155.
6. Kohanski M A, DePristo M A, Collins J J. Sublethal Antibiotic Treatment Leads to Multidrug Resistance via Radical-Induced Mutagenesis. Molecular Cell 2010; 37:311-320.
7. Christner M, Rohde H, Wolters M, Sobottka I, Wegscheider K, Aepfelbacher M. Rapid identification of bacteria from positive blood culture bottles by use of matrix-assisted laser desorption-ionization time of flight mass spectrometry fingerprinting. J Clin Microbiol 2010; 48:1584-91.
8. Sauer S, Kliem M. Mass spectrometry tools for the classification and identification of bacteria. Nat Rev Microbiol 2010; 8:74-82.
9. Carey J R, Suslick K S, Hulkower K I, Imlay J A, Imlay K R C, Ingison C K, Ponder J B, Sen A, Wittrig A E. Rapid Identification of Bacteria with a Disposable Colorimetric Sensing Array.
Journal of the American Chemical Society 2011; 133: 7571-7576.
10. Barczak A K, Gomez J E, Kaufmann B B, Hinson E R, Cosimi L, Borowsky M L, Onderdonk A B, Stanley S A, Kaur D, Bryant K F and others. RNA signatures allow rapid identification of pathogens and antibiotic susceptibilities. Proc Natl Acad Sci USA 2012; 109:6217-22.
11. Huletsky A, Giroux R, Rossbach V, Gagnon M, Vaillancourt M, Bernier M, Gagnon F, Truchon K, Bastien M, Picard F J and others. New Real-Time PCR Assay for Rapid Detection of Methicillin-Resistant *Staphylococcus aureus* Directly from Specimens Containing a Mixture of Staphylococci. Journal of Clinical Microbiology 2004; 42:1875-1884.

12. CLSI. M100-S26 Performace Standards for Antimicrobial Susceptibility Testing; 2016.
13. Mason D J, Allman R, Stark J M, Lloyd D. Rapid estimation of bacterial antibiotic susceptibility with flow cytometry. Journal of Microscopy 1994; 176:8-16.
14. Walberg M, Gaustad P, Steen H B. Rapid flow cytometric assessment of mecillinam and ampicillin bacterial susceptibility. Journal of Antimicrobial Chemotherapy 1996; 37:1063-1075.
15. Walberg M, Gaustad P, Steen H B. Rapid assessment of ceftazidime, ciprofloxacin, and gentamicin susceptibility in exponentially-growing *E. coli* cells by means of flow cytometry. Cytometry 1997; 27:169-178.
16. Suller M T E, Lloyd D. Fluorescence monitoring of antibiotic-induced bacterial damage using flow cytometry. Cytometry 1999; 35:235-241.
17. Mortimer F C, Mason D J, Gant V A. Flow Cytometric Monitoring of Antibiotic-Induced Injury in *Escherichia coli* Using Cell-Impermeant Fluorescent Probes. Antimicrobial Agents and Chemotherapy 2000; 44:676-681.
18. Walberg M, Steent H B. flow cytometric monitoring of bacterial susceptibility to antibiotics. In: Zbigniew Darzynkiewicz HACJPR, editor. Methods in Cell Biology. Volume Volume 64, Part B: Academic Press; 2001. p 553-566.
19. Gauthier C, St-Pierre Y, Villemur R. Rapid antimicrobial susceptibility testing of urinary tract isolates and samples by flow cytometry. Journal of Medical Microbiology 2002; 51:192-200.
20. Assunção P, Antunes N T, Rosales R S, Poveda C, De La Fe C, Poveda J B, Davey H M. Application of flow cytometry for the determination of minimal inhibitory concentration of several antibacterial agents on *Mycoplasma hyopneumoniae*. Journal of Applied Microbiology 2007; 102:1132-1137.
21. Faria-Ramos I, Espinar M J, Rocha R, Santos-Antunes J, Rodrigues A G, Cantón R, Pina-Vaz C. A novel flow cytometric assay for rapid detection of extended-spectrum beta-lactamases. Clinical Microbiology and Infection 2013; 19:E8-E15.
22. Nuding S, Zabel T L. Detection, Identification and Susceptibility Testing of Bacteria by Flow Cytometry. J Bacteriol Parasitol 2013; S5:005.
23. Shapiro H M. Multiparameter flow cytometry of bacteria: Implications for diagnostics and therapeutics. Cytometry 2001; 43:223-226.
24. Dietzman D E, Fischer G W, Schoenknecht F D. Neonatal *Escherichia coli* septicemia-bacterial counts in blood. The Journal of Pediatrics 1974; 85:128-130.
25. Yagupsky P, Nolte F S. Quantitative aspects of septicemia. Clinical Microbiology Reviews 1990; 3:269-279.
26. Mansour J D, Robson J A, Arndt C W, Schulte T H. Detection of *Escherichia coli* in blood using flow cytometry. Cytometry 1985; 6:186-90.
27. Pitt W G, Alizadeh M, Husseini G A, McClellan D S, Buchanan C M, Bledsoe C G, Robison R A, Blanco R, Roeder B L, Melville M and others. Rapid separation of bacteria from blood-review and outlook. Biotechnol Prog 2016; 32:823-39.
28. Hou H W, Bhattacharyya R P, Hung D T, Han J. Direct detection and drug-resistance profiling of bacteremias using inertial microfluidics. Lab Chip 2015; 15:2297-307.
29. Tay A, Pavesi A, Yazdi S R, Lim C T, Warkiani M E. Advances in microfluidics in combating infectious diseases. Biotechnology Advances 2016; 34:404-421.
30. Gosiewski T, Szala L, Pietrzyk A, Brzychczy-Wloch M, Heczko P B, Bulanda M. Comparison of methods for isolation of bacterial and fungal DNA from human blood. Curr Microbiol 2014; 68:149-55.

31. Gosiewski T, Jurkiewicz-Badacz D, Sroka A, Brzychczy-Włoch M, Bulanda M. A novel, nested, multiplex, real-time PCR for detection of bacteria and fungi in blood. BMC Microbiology 2014; 14:144.

32. Steinberger-Levy I, Zahavy E, Cohen S, Flashner Y, Mamroud E, Aftalion M, Gur D, Ber R. Enrichment of *Yersinia pestis* from blood cultures enables rapid antimicrobial susceptibility determination by flow cytometry. Adv Exp Med Biol 2007; 603:339-50.

33. Doern G V, Vautour R, Gaudet M, Levy B. Clinical impact of rapid in vitro susceptibility testing and bacterial identification. Journal of Clinical Microbiology 1994; 32:1757-1762.

34. Gogelein H, Huby A. Interaction of saponin and digitonin with black lipid membranes and lipid monolayers. Biochim Biophys Acta 1984; 773:32-8.

35. Francis G, Kerem Z, Makkar H P, Becker K. The biological action of saponins in animal systems: a review. Br J Nutr 2002; 88:587-605.

36. Arabski M, Wegierek-Ciuk A, Czerwonka G, Lankoff A, Kaca W. Effects of Saponins against Clinical *E. coli* Strains and Eukaryotic Cell Line. Journal of Biomedicine and Biotechnology 2012; 2012:6.

37. Roederer M, Moore W, Treister A, Hardy R R, Herzenberg L A. Probability binning comparison: a metric for quantitating multivariate distribution differences. Cytometry 2001; 45:47-55.

38. Roederer M, Treister A, Moore W, Herzenberg L A. Probability binning comparison: A metric for quantitating univariate distribution differences. Cytometry 2001; 45:37-46.

39. Beecks C, Uysal M S, Seidl T. Signature quadratic form distances for content-based similarity. Proceedings of the 17th ACM international conference on Multimedia. Beijing, China: ACM; 2009. p 697-700.

40. Beecks C, Uysal M S, Seidl T. Signature Quadratic Form Distance. Proceedings of the ACM International Conference on Image and Video Retrieval. Xi'an, China: ACM; 2010. p 438-445.

41. Zeitschrift fir Astronomie und verwandte Wissenschaften: J. G. Cotta; 1816.

42. Ruppert D. Statistics and Data Analysis for Financial Engineering: Springer; 2010.

43. Chaudhuri P. On a Geometric Notion of Quantiles for Multivariate Data. Journal of the American Statistical Association 1996; 91:862-872.

44. Dennis Jr J E, Schnabel R B. Numerical methods for unconstrained optimization and nonlinear equations: Siam; 1996.

45. Deen J, von Seidlein L, Andersen F, Elle N, White N J, Lubell Y. Community-acquired bacterial bloodstream infections in developing countries in south and southeast Asia: a systematic review. Lancet Infect Dis 2012; 12:480-7.

46. Vincent J L, Rello J, Marshall J, Silva E, Anzueto A, Martin C D, Moreno R, Lipman J, Gomersall C, Sakr Y and others. International study of the prevalence and outcomes of infection in intensive care units. Jama 2009; 302:2323-9.

What is claimed is:

1. A method comprising:

recovering and concentrating bacteria with an unknown bacterial identity from an infected bodily fluid sample from a subject, without culture-based amplification;

dividing the infected bodily fluid sample from the subject into samples for incubation with an antibiotic and a paired control sample that is not incubated with any antibiotic;

collecting multidimensional data via label-free light scatter flow cytometry of the infected bodily fluid samples incubated with the antibiotic and the paired control sample;

analyzing the multidimensional data to determine if bacteria in one or more of the infected bodily fluid samples is susceptible to the antibiotic; and treating the subject with a therapeutically effective amount of an antibiotic based on determining, from the analyzing, that the bacteria in at least one of the infected bodily fluid samples is susceptible to the antibiotic.

2. The method of claim 1 further comprising:
prior to the dividing,
diluting the infected bodily fluid sample with a bacterial growth medium;
treating the infected bodily fluid sample with saponin; and
incubating the infected bodily fluid sample to allow for bacterial growth.

3. The method of claim 1, wherein the method is selected from the group consisting of:
a method for rapidly determining the antibiotic susceptibility of bacteria in the subject's bodily fluid sample;
a method for rapidly detecting the antibiotic susceptibility of bacteria in the subject's bodily fluid sample;
a method for rapidly differentiating between the antibiotic susceptibilities of different bacteria in the subject's bodily fluid sample;
a method for rapidly diagnosing the subject with antibiotic-susceptible bacteria or antibiotic-resistant bacteria in the subject's bodily fluid sample; and
a method for rapidly classifying bacteria in the subject's bodily fluid sample as being susceptible to the antibiotic or not susceptible to the antibiotic.

4. A method comprising:
treating a sample of a bodily fluid from a subject infected by bacteria with an unknown bacterial identity with saponin;
amplifying the bacteria with culture-based amplification;
dividing the infected bodily fluid sample treated with saponin into samples for incubation with an antibiotic and a paired control sample that is not incubated with any antibiotic;
collecting multidimensional data via label-free light scatter flow cytometry of the infected bodily fluid samples incubated with the antibiotic and the paired control sample;
analyzing the multidimensional data to determine if bacteria in one or more of the infected bodily fluid samples is susceptible to the antibiotic;
calculating an adaptive, multidimensional Probability Binned-signature Quadratic Form (PB-SQF) statistical distance for each of the infected bodily fluid samples incubated with the antibiotic and the paired control sample based on the results of the label-free flow cytometry analysis;
comparing the statistical distance from the infected bodily fluid samples incubated with the antibiotic to the paired control sample;
determining whether bacteria in any one of the infected bodily fluid samples is susceptible to the antibiotic; and treating the subject with a therapeutically effective amount of an antibiotic based on determining that the bacteria in at least one of the infected bodily fluid samples is susceptible to the antibiotic.

5. The method according to claim 1 further comprising treating the infected bodily fluid sample with saponin;
wherein treating the infected bodily fluid sample with saponin and incubating the diluted infected bodily fluid sample allow for bacterial growth/expansion to occur at 37° C.

6. The method according to claim 1 further comprising prior to the dividing; treating the infected bodily fluid sample with saponin for at least about 10 minutes.

7. The method according to claim 1 further comprising prior to the dividing; treating the infected bodily fluid sample with saponin for at most about 45 minutes.

8. The method according to claim 1 further comprising treating the infected bodily fluid sample with saponin;
wherein treating the infected bodily fluid sample with saponin and incubating the diluted infected bodily fluid sample allow for bacterial growth/expansion simultaneously or substantially simultaneously.

9. The method according to claim 8, wherein simultaneous or substantially simultaneous saponin lysis and incubation last for about 0.5 hours to about 5 hours.

10. The method according to claim 8, wherein simultaneous or substantially simultaneous saponin lysis and incubation last for about 0.5 hours to about 2 hours.

11. The method according to claim 2 further comprising:
isolating the infected bodily fluid sample from the subject prior to the diluting;
calculating an adaptive, multidimensional Probability Binned-signature Quadratic Form (PB-sQF) statistical distance for each of the infected bodily fluid samples incubated with the antibiotic and the paired control sample based on the results of the flow cytometry analysis;
comparing the statistical distance from the patient's infected bodily fluid samples incubated with the antibiotic to the paired control sample; and
determining whether bacteria in any one of the infected bodily fluid samples is susceptible to the antibiotic.

12. The method according to claim 11, wherein determining antibiotic susceptibility lasts for about 0.5 hours to about 5 hours.

13. The method according to claim 11, wherein determining antibiotic susceptibility lasts for about 0.5 hours to about 2 hours.

14. A method comprising:
recovering and concentrating bacteria with an unknown bacterial identity from an infected bodily fluid sample from a subject, without culture-based amplification;
treating the infected bodily fluid sample with saponin;
dividing the infected bodily fluid sample treated with saponin into samples for incubation with an antibiotic and a paired control sample that is not incubated with any antibiotic;
collecting multidimensional data including forward and side scatter via dye-free flow cytometry of the infected bodily fluid samples incubated with the antibiotic and the paired control sample;
analyzing the multidimensional data to determine if bacteria in one or more of the infected bodily fluid samples is susceptible to the antibiotic; and treating the subject with a therapeutically effective amount of an antibiotic based on determining, from the analyzing, that the bacteria in at least one of the infected bodily fluid samples is susceptible to the antibiotic.

\* \* \* \* \*